(12) United States Patent
Scheib et al.

(10) Patent No.: US 11,745,031 B2
(45) Date of Patent: Sep. 5, 2023

(54) SURGICAL INSTRUMENT WITH MULTI-FUNCTIONING TRIGGER

(71) Applicant: Cilag GmbH International, Zug (CH)

(72) Inventors: Charles J. Scheib, Loveland, OH (US); Benjamin M. Boyd, Fairborn, OH (US); Paul F. Riestenberg, North Bend, OH (US); Craig N. Faller, Batavia, OH (US); Allison Hamilton, Cincinnati, OH (US); Patrick J. Swindon, Santa Clara, CA (US); Christopher J. Chermside-Scabbo, St. Louis, MO (US); Kevin L. Houser, Springboro, OH (US); David J. Cagle, Cincinnati, OH (US); Geoffrey S. Strobl, Williamsburg, OH (US); Benjamin J. Danziger, Kenmore, WA (US); Rudolph H. Nobis, Mason, OH (US)

(73) Assignee: Cilag GmbH International, Zug (CH)

( * ) Notice: Subject to any disclaimer, the term of this patent is extended or adjusted under 35 U.S.C. 154(b) by 599 days.

(21) Appl. No.: 16/784,428

(22) Filed: Feb. 7, 2020

(65) Prior Publication Data
US 2020/0246642 A1  Aug. 6, 2020

Related U.S. Application Data

(63) Continuation of application No. 14/972,920, filed on Dec. 17, 2015, now abandoned.

(51) Int. Cl.
*A61B 18/12* (2006.01)
*A61N 7/02* (2006.01)
(Continued)

(52) U.S. Cl.
CPC ........ *A61N 7/02* (2013.01); *A61B 17/320092* (2013.01); *A61B 2017/00137* (2013.01);
(Continued)

(58) Field of Classification Search
CPC ........ A61B 17/320092; A61B 18/1442; A61B 2017/320093; A61B 2017/320094;
(Continued)

(56) References Cited

U.S. PATENT DOCUMENTS

| 4,911,159 A | 3/1990 | Johnson et al. |
| 5,269,780 A | 12/1993 | Roos |

(Continued)

FOREIGN PATENT DOCUMENTS

| CN | 102232853 A | 11/2011 |
| CN | 102497827 A | 6/2012 |

(Continued)

OTHER PUBLICATIONS

Chinese Office Action and Search Report dated Jun. 3, 2020 for Application No. 201680073879.X, 11 pages.

(Continued)

*Primary Examiner* — Daniel W Fowler
(74) *Attorney, Agent, or Firm* — Frost Brown Todd LLP

(57) ABSTRACT

A surgical instrument includes an end effector and a handle assembly. The end effector is configured to operate at a first energy level and at a second energy level. The end effector is further configured to transition between an open position and a closed position. The end effector is configured to grasp tissue in the closed position. The handle assembly includes a body, a trigger, and an activation element. The trigger is configured to pivot in a first direction relative to the body to actuate the end effector from the open position to the closed position. The activation element is configured to activate the end effector at either the first energy level or the second energy level. The trigger is configured to either activate the activation element or determine whether the end effector operates at the first energy level or the second energy level.

12 Claims, 23 Drawing Sheets

(51) Int. Cl.
*A61B 17/32* (2006.01)
*A61B 18/00* (2006.01)
*A61N 7/00* (2006.01)
*A61B 17/00* (2006.01)

(52) U.S. Cl.
CPC ............... *A61B 2017/00181* (2013.01); *A61B 2017/00367* (2013.01); *A61B 2017/00411* (2013.01); *A61B 2017/320093* (2017.08); *A61B 2017/320094* (2017.08); *A61B 2017/320095* (2017.08); *A61B 2018/0063* (2013.01); *A61B 2018/00595* (2013.01); *A61B 2018/00619* (2013.01); *A61N 2007/0056* (2013.01)

(58) Field of Classification Search
CPC ......... A61B 2017/320095; A61B 2018/00595; A61B 2018/00619; A61B 2018/0063
See application file for complete search history.

(56) References Cited

U.S. PATENT DOCUMENTS

| | | |
|---|---|---|
| 5,322,055 A | 6/1994 | Davison et al. |
| 5,324,299 A | 6/1994 | Davison et al. |
| 5,873,873 A | 2/1999 | Smith et al. |
| 5,980,510 A | 11/1999 | Tsonton et al. |
| 6,214,003 B1 | 4/2001 | Morgan et al. |
| 6,270,497 B1 | 8/2001 | Sekino et al. |
| 6,283,981 B1 | 9/2001 | Beaupre |
| 6,309,400 B2 | 10/2001 | Beaupre |
| 6,325,811 B1 | 12/2001 | Messerly |
| 6,423,082 B1 | 7/2002 | Houser et al. |
| 6,666,875 B1 | 12/2003 | Sakurai et al. |
| 6,773,444 B2 | 8/2004 | Messerly |
| 6,783,524 B2 | 8/2004 | Anderson et al. |
| 8,057,498 B2 | 11/2011 | Robertson |
| 8,461,744 B2 | 6/2013 | Wiener et al. |
| 8,591,536 B2 | 11/2013 | Robertson |
| 8,623,027 B2 | 1/2014 | Price et al. |
| 8,663,220 B2 | 5/2014 | Wiener et al. |
| 8,911,460 B2 | 12/2014 | Neurohr et al. |
| 8,986,302 B2 | 3/2015 | Aldridge et al. |
| 9,023,071 B2 | 5/2015 | Miller et al. |
| 9,044,243 B2 | 6/2015 | Johnson et al. |
| 9,095,367 B2 | 8/2015 | Olson et al. |
| 9,468,454 B2 | 10/2016 | Johnson et al. |
| 9,649,150 B2 | 5/2017 | Houser et al. |
| 9,943,325 B2 | 4/2018 | Faller et al. |
| 2002/0115917 A1 | 8/2002 | Honda et al. |
| 2006/0079874 A1 | 4/2006 | Faller et al. |
| 2006/0089636 A1 | 4/2006 | Christopherson et al. |
| 2007/0011713 A1 | 1/2007 | Abramson et al. |
| 2007/0191713 A1 | 8/2007 | Eichmann et al. |
| 2007/0260238 A1 | 11/2007 | Guerra |
| 2007/0282333 A1 | 12/2007 | Fortson et al. |
| 2008/0200940 A1 | 8/2008 | Eichmann et al. |
| 2011/0009890 A1* | 1/2011 | Palmer ................. H01H 13/64 606/169 |
| 2011/0015660 A1 | 1/2011 | Wiener et al. |
| 2011/0054469 A1 | 3/2011 | Kappus et al. |
| 2011/0087219 A1* | 4/2011 | Boudreaux ........ A61B 18/1445 606/41 |
| 2011/0264093 A1 | 10/2011 | Schall |
| 2012/0112687 A1 | 5/2012 | Houser et al. |
| 2012/0116265 A1 | 5/2012 | Houser et al. |
| 2012/0116391 A1 | 5/2012 | Houser et al. |
| 2013/0053831 A1* | 2/2013 | Johnson ............... A61B 18/085 606/1 |
| 2013/0304066 A1 | 11/2013 | Kerr et al. |
| 2014/0005701 A1 | 1/2014 | Olson et al. |
| 2014/0025053 A1 | 1/2014 | Nau, Jr. et al. |
| 2014/0257285 A1* | 9/2014 | Moua ................. A61B 17/282 606/52 |
| 2014/0277029 A1* | 9/2014 | Messerly ....... A61B 17/320092 606/169 |
| 2015/0080924 A1 | 3/2015 | Stulen et al. |
| 2015/0141981 A1 | 5/2015 | Price et al. |
| 2015/0150581 A1* | 6/2015 | Van Tol ............ A61B 18/1445 606/34 |
| 2017/0172614 A1 | 6/2017 | Scheib et al. |

FOREIGN PATENT DOCUMENTS

| | | |
|---|---|---|
| EP | 1842502 A1 | 10/2007 |
| JP | 2000-271144 A | 10/2000 |
| WO | WO 2007/014215 A2 | 2/2007 |

OTHER PUBLICATIONS

International Search Report and Written Opinion dated May 31, 2017 for International Application No. PCT/US2016/066468, 23 pages.
Japanese Notification of Reasons for Refusal dated Nov. 24, 2020 for Application No. 2018-531501, 5 pages.
U.S. Appl. No. 61/410,603, filed Nov. 5, 2010.

* cited by examiner

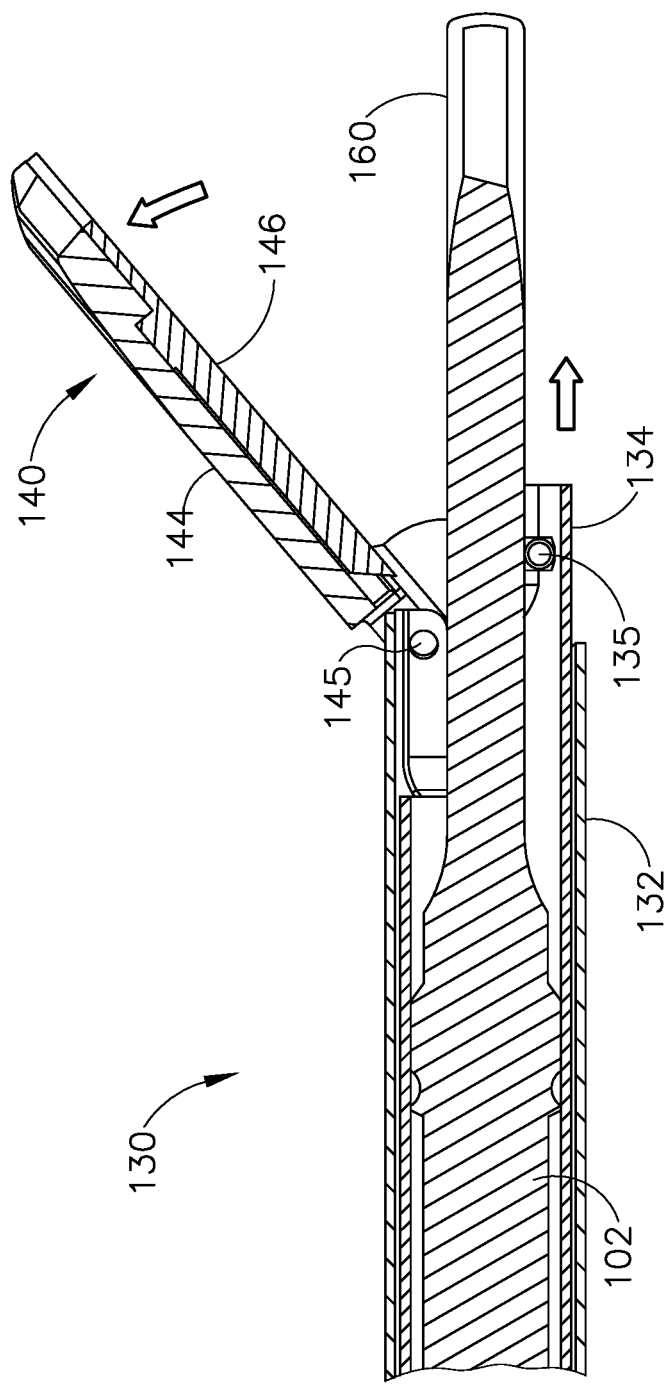

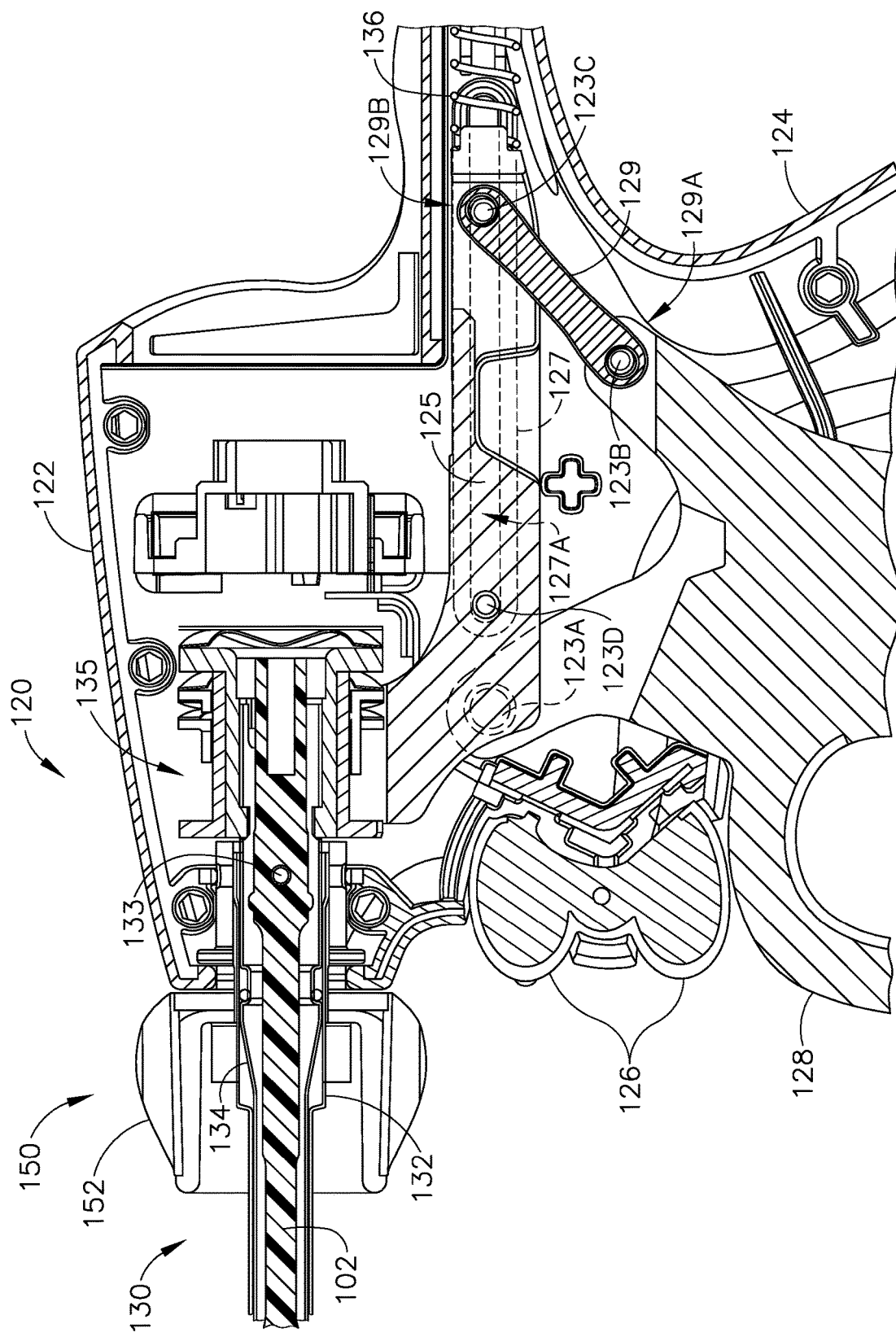

SURGICAL INSTRUMENT WITH MULTI-FUNCTIONING TRIGGER

This application is a continuation of U.S. patent application Ser. No. 14/972,920, entitled "Surgical Instrument with Multi-Functioning Trigger," filed Dec. 17, 2015, published as U.S. Pub. No. 2017/0172614 on Jun. 22, 2017, now abandoned.

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. Some instruments have a clamp arm and clamp pad for grasping tissue with the blade element.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Clamp pad for Use with an Ultrasonic Surgical Instrument," published Apr. 13, 2006, now abandoned the disclosure of which is incorporated by reference herein; U.S. Pub. No. 2007/0191713, entitled "Ultrasonic Device for Cutting and Coagulating," published Aug. 16, 2007, now abandoned the disclosure of which is incorporated by reference herein; U.S. Pub. No. 2007/0282333, entitled "Ultrasonic Waveguide and Blade," published Dec. 6, 2007, now abandoned the disclosure of which is incorporated by reference herein; U.S. Pub. No. 2008/0200940, entitled "Ultrasonic Device for Cutting and Coagulating," published Aug. 21, 2008, now abandoned the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2014, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; and U.S. Pub. No. 2014/0114334, published Apr. 24, 2014, issued as U.S. Pat. No. 9,095,367 on Aug. 4, 2015, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 4 depicts a cross-sectional side view of the end effector of FIG. 3 in an open configuration;

FIG. 5 depicts a cross-sectional side view of a handle assembly of the instrument of FIG. 2;

Figure 1:
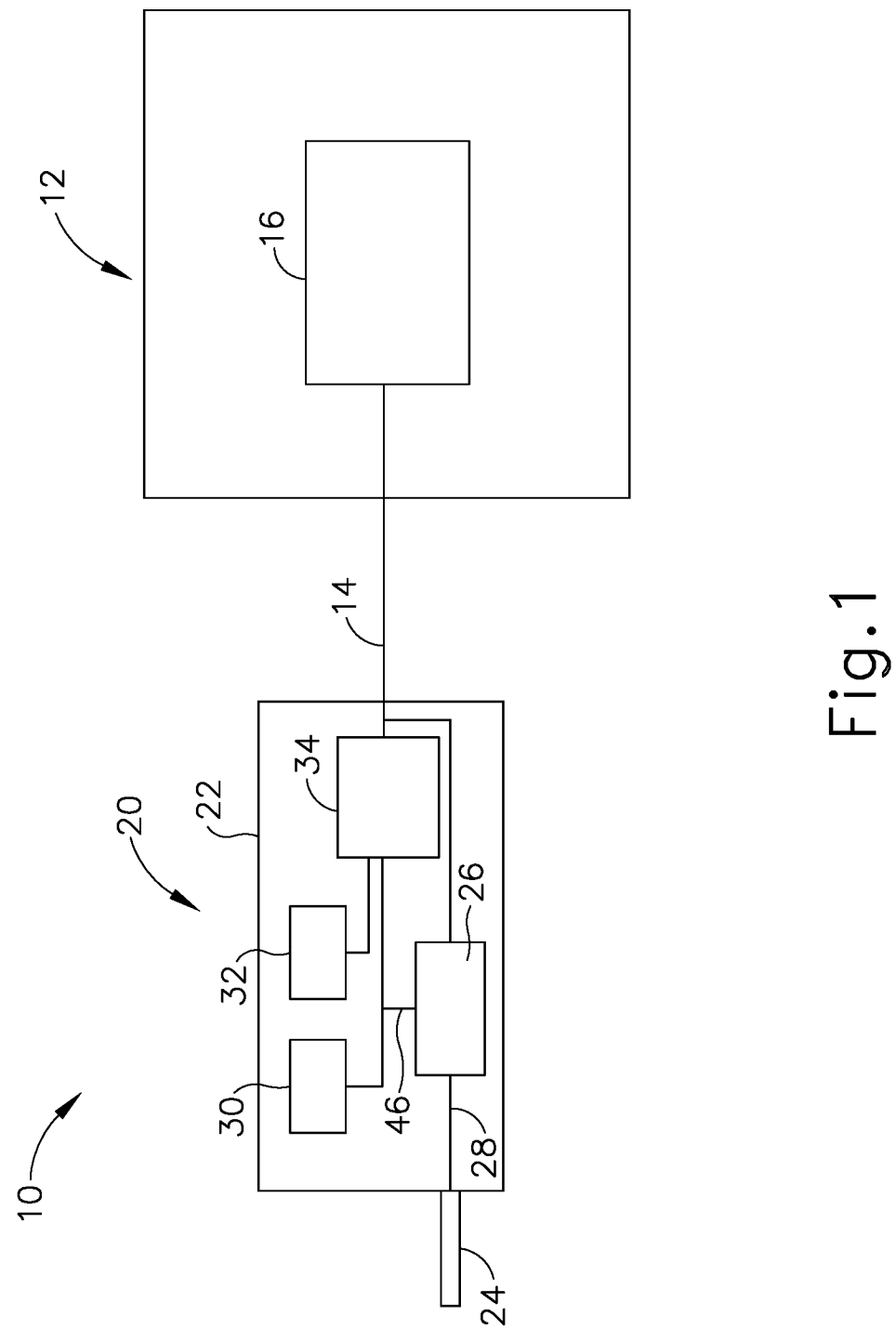
FIG. 1 depicts a block schematic view of an exemplary surgical system.
Figure 2:
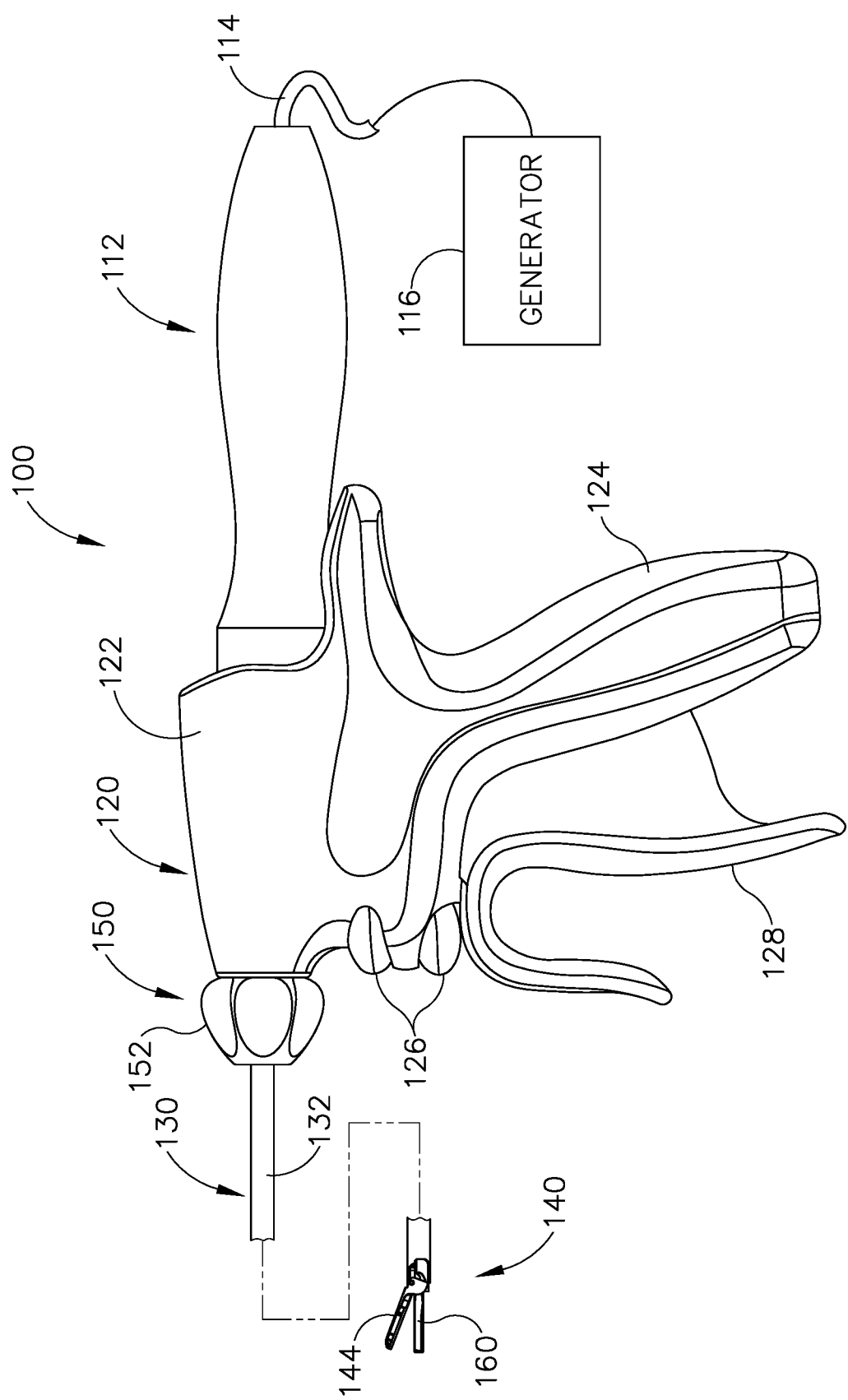
FIG. 2 depicts a side elevational view of an exemplary surgical instrument that may be incorporated into the system of FIG. 1.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers to the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via a cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04, GEN11, or GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Alternatively, any other suitable generator may be used. As will be described in greater detail below, generator (12) is operable to provide power to instrument (20) to perform ultrasonic surgical procedures.

Instrument (20) comprises a handle assembly (22), which is configured to be grasped in one hand (or two hands) of an operator and manipulated by one hand (or two hands) of the operator during a surgical procedure. For instance, in some versions, handle assembly (22) may be grasped like a pencil by the operator. In some other versions, handle assembly (22) may include a scissor grip that may be grasped like scissors by the operator. In some other versions, handle assembly (22) may include a pistol grip that may be grasped like a pistol by the operator. Of course, handle assembly (22) may be configured to be gripped in any other suitable fashion. Furthermore, some versions of instrument (20) may substitute handle assembly (22) with a body that is coupled to a robotic surgical system that is configured to operate instrument (20) (e.g., via remote control, etc.). In the present example, a blade (24) extends distally from handle assembly (22). Handle assembly (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handle assembly (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths ($n\lambda/2$). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handle assembly (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of the generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handle assembly (22). For instance, in some such versions, generator (12) only communicates one type of electrical power (e.g., just one voltage and/or current available) to handle assembly (22), and control circuitry (16) within handle assembly (22) is operable to modify the electrical power (e.g., the voltage of the electrical power), in accordance with selections made by the operator via control selector (30), before the electrical power reaches ultrasonic transducer (26). Furthermore, generator (12) may be incorporated into handle assembly (22) along with all other components of surgical system (10). For instance, one or more batteries (not shown) or other portable sources of power may be provided in handle assembly (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instrument

The following discussion relates to various exemplary components and configurations of surgical instrument (20). It should be understood that the various examples of surgical instrument (20) described below may be readily incorporated into surgical system (10) as described above. It should also be understood that the various components and operabilities of surgical instrument (20) described above may be readily incorporated into the exemplary versions of surgical instrument (20) described below. Various suitable ways in which the above and below teachings may be combined will be apparent to those of ordinary skill in the art in view of the teachings herein. It should also be understood that the below teachings may be readily combined with the various teachings of the references that are cited herein.

FIGS. 2-5 illustrate an exemplary ultrasonic surgical instrument (100). At least part of surgical instrument (100) may be constructed and operable in accordance with at least some of the teachings of U.S. Pat. Nos. 5,322,055; 5,873,873; 5,980,510; 6,325,811; 6,773,444; 6,783,524; 8,461,744; 8,623,027; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2014/0114334, issued as U.S. Pat. No. 9,095,367 on Aug. 4, 2015; U.S. Pat. App. No. 61/410,603; and/or U.S. patent application Ser. No. 14/028,717, issued as U.S. Pat. No. 10,172,636 on Jan. 8, 2019. The disclosures of each of the foregoing patents, publications, and applications are incorporated by reference herein. As described therein and as will be described in greater detail below, surgical instrument (100) is operable to cut tissue and seal or weld tissue (e.g., a blood vessel, etc.) substantially simultaneously. It should also be understood that surgical instrument (100) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, surgical instrument (100) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to surgical instrument (100), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Surgical instrument (100) of the present example comprises a handle assembly (120), a shaft assembly (130), and an end effector (140). Handle assembly (120) comprises a body (122) including a pistol grip (124) and a pair of buttons (126). Handle assembly (120) also includes a trigger (128) that is pivotable toward and away from pistol grip (124). It should be understood, however, that various other suitable configurations may be used, including but not limited to a pencil-grip configuration or a scissor-grip configuration. End effector (140) includes an ultrasonic blade (160) and a pivoting clamp arm (144). Clamp arm (144) is coupled with trigger (128) such that clamp arm (144) is pivotable toward ultrasonic blade (160) in response to pivoting of trigger (128) toward pistol grip (124); and such that clamp arm (144) is pivotable away from ultrasonic blade (160) in response to pivoting of trigger (128) away from pistol grip (124). Various suitable ways in which clamp arm (144) may be coupled with trigger (128) will be apparent to those of ordinary skill in the art in view of the teachings herein. In some versions, one or more resilient members are used to bias clamp arm (144) and/or trigger (128) to the open position shown in FIG. 4.

An ultrasonic transducer assembly (112) extends proximally from body (122) of the handle assembly (120). Transducer assembly (112) is coupled with a generator (116) via a cable (114). Transducer assembly (112) receives electrical power from generator (116) and converts that power into ultrasonic vibrations through piezoelectric principles. Generator (116) may include a power source and control module configured to provide a power profile to transducer assembly (112) that is particularly suited for the generation of ultrasonic vibrations through transducer assembly (112). By way of example only, generator (116) may comprise a GEN 300 sold by Ethicon Endo-Surgery, Inc. of Cincinnati, Ohio. In addition or in the alternative, generator (116) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

Blade (160) of the present example is operable to vibrate at ultrasonic frequencies in order to effectively cut through and seal tissue, particularly when the tissue is being clamped between clamp arm (144) and blade (160). Blade (160) is positioned at the distal end of an acoustic drivetrain. This acoustic drivetrain includes transducer assembly (112) and an acoustic waveguide (102). Transducer assembly (112) includes a set of piezoelectric discs (not shown) located proximal to a horn (not shown) of the rigid acoustic waveguide (102). The piezoelectric discs are operable to convert electrical power into ultrasonic vibrations, which are then transmitted along acoustic waveguide (102), which extends through shaft assembly (130), to blade (160) in accordance with known configurations and techniques. By way of example only, this portion of the acoustic drivetrain may be configured in accordance with various teachings of various references that are cited herein.

Waveguide (102) is secured within shaft assembly (130) via a pin (133), which passes through waveguide (102) and shaft assembly (130). Pin (133) is located at a position along the length of waveguide (102) corresponding to a node associated with resonant ultrasonic vibrations communicated through waveguide (102). When ultrasonic blade (160) is in an activated state (i.e., vibrating ultrasonically), ultrasonic blade (160) is operable to effectively cut through and seal tissue, particularly when the tissue is being clamped between clamp arm (144) and ultrasonic blade (160). It should be understood that waveguide (102) may be configured to amplify mechanical vibrations transmitted through waveguide (102). Furthermore, waveguide (102) may include features operable to control the gain of the longitudinal vibrations along waveguide (102) and/or features to tune waveguide (102) to the resonant frequency of the system.

In the present example, the distal end of blade (160) is located at a position corresponding to an anti-node associated with resonant ultrasonic vibrations communicated through waveguide (102), in order to tune the acoustic assembly to a preferred resonant frequency $f_o$ when the acoustic assembly is not loaded by tissue. When transducer assembly (112) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (112) of the present example is activated, these mechanical oscillations are transmitted through waveguide (102) to reach blade (160), thereby providing oscillation of blade (160) at the resonant ultrasonic frequency. Thus, when tissue is secured between blade (160) and clamp arm (144), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (144) to also cauterize the tissue. While some configurations for an acoustic transmission assembly and transducer assembly (112) have been described, still other suitable configurations for an acoustic transmission assembly and transducer assembly (112) will be apparent to one or ordinary skill in the art in view of the teachings herein. Similarly, other suitable configurations for end effector (140) will be apparent to those of ordinary skill in the art in view of the teachings herein.

An operator may activate buttons (126) to selectively activate transducer assembly (112) to activate blade (160). In the present example, two buttons (126) are provided—one for activating blade (160) at a low power and another for activating blade (160) at a high power. However, it should be understood that any other suitable number of buttons and/or otherwise selectable power levels may be provided. For instance, a foot pedal may be provided to selectively activate transducer assembly (112). Buttons (126) of the present example are positioned such that an operator may readily fully operate instrument (100) with a single hand. For instance, the operator may position their thumb about pistol grip (124), position their middle, ring, and/or little finger about trigger (128), and manipulate buttons (126) using their index finger. Of course, any other suitable techniques may be used to grip and operate surgical instrument (100); and buttons (126) may be located at any other suitable positions.

Shaft assembly (130) of the present example comprises an outer sheath (132), an inner tube (134) slidably disposed within the outer sheath (132), and a waveguide (102) disposed within the inner tube (134). As will be discussed in more detail below, inner tube (134) is operable to translate longitudinally within outer sheath (132) relative to outer sheath (132) to selectively pivot clamp arm (144) toward and away from blade (160). Shaft assembly (130) of the present example further includes a rotation assembly (150). Rotation assembly (150) is operable to rotate the entire shaft assembly (130) and end effector (140) relative to handle assembly (120) about a longitudinal axis of shaft assembly (130). In some versions, rotation assembly (150) is operable to selectively lock the angular position of shaft assembly (130) and end effector (140) relative to handle assembly (120) about the longitudinal axis of shaft assembly (130). For instance, a rotation knob (152) of rotation assembly (150) may be translatable between a first longitudinal position, in which shaft assembly (130) and end effector (140) are rotatable relative to handle assembly (120) about the longitudinal axis of shaft assembly (130); and a second longitudinal position, in which shaft assembly (130) and end effector (140) are not rotatable relative to handle assembly (120) about the longitudinal axis of shaft assembly (130). Of course, shaft assembly (130) may have a variety of other components, features, and operabilities, in addition to or in lieu of any of those noted above. Other suitable configurations for shaft assembly (130) will be apparent to those of ordinary skill in the art in view of the teachings herein.

Figure 3:
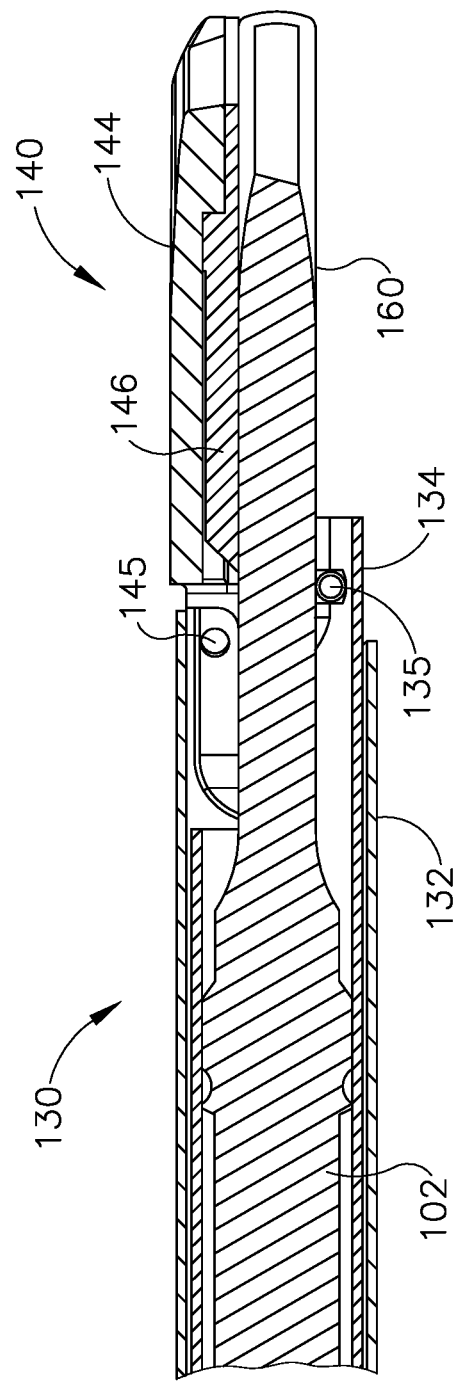
FIG. 3 depicts a cross-sectional side view of an end effector of the instrument of FIG. 2 in a closed configuration.

As shown in FIGS. 3 and 4, end effector (140) includes ultrasonic blade (160) and clamp arm (144). Clamp arm (144) includes a clamp pad (146) secured to an underside of the clamp arm (144) and facing the blade (160). Clamp arm (144) is pivotably coupled with a distal end of outer sheath (132) of shaft assembly (130) above ultrasonic blade (160) via a pin (145). As best seen in FIG. 4, a distal end of inner tube (134) is rotatably coupled with a proximal end of clamp arm (144) below ultrasonic blade (160) via a pin (135) such that longitudinal translation of inner tube (134) causes rotation of clamp arm (144) about pin (145) toward and away from ultrasonic blade (160) to thereby clamp tissue between clamp arm (144) and ultrasonic blade (160) to cut and/or seal the tissue. In particular, proximal longitudinal translation of inner tube (134) relative to outer sheath (132) and handle assembly (120) causes clamp arm (144) to move toward ultrasonic blade (160); and distal longitudinal translation of inner tube (134) relative to outer sheath (132) and handle assembly (120) causes clamp arm (144) to move away from ultrasonic blade (160).

As shown in FIG. 5, and as discussed above, trigger (128) is pivotably coupled to handle assembly (120) via a pin (123A) such that trigger (128) is operable to rotate about pin (123A). As will be described in more detail below, trigger (128) is coupled with a yoke (125) via a linkage (129) such that rotation of trigger (128) about pin (123A) causes longitudinal translation of yoke (125). A first end (129A) of linkage (129) is rotatably coupled with a proximal portion of trigger (128) via a pin (123B). A second end (129B) of linkage (129) is rotatably coupled with a proximal portion of yoke (125) via a pin (123C). A pair of elongate oval-shaped projections (127) extend inwardly from interior surfaces of body (122). An interior surface of each oval-shaped projection (127) defines an elongate oval-shaped slot (127A). Pin (123C) passes completely through the proximal portion of yoke (125) and second end (129B) of linkage (129) such that ends of pin (123C) extend from opposite sides of yoke (125). These ends of pin (123C) are slidably and rotatably disposed within oval-shaped slots (127A). A pin (123D) passes completely through a distal portion of yoke (125) such that ends of pin (123D) extend from opposite sides of yoke (125). These ends of pin (123D) are slidably and rotatably disposed within oval-shaped slots (127A). It should therefore be understood that yoke (125) is longitudinally translatable within oval-shaped slots (127A) via pins (123C, 123D) between a proximal longitudinal position and a distal longitudinal position. Furthermore, because the proximal portion of trigger (128) is coupled with yoke (125) via linkage (129), pivoting of trigger (128) toward and away from pistol grip (124) will cause longitudinal translation of yoke (125) within oval-shaped slots (127A). In particular, pivoting of trigger (128) toward pistol grip (124) will cause proximal longitudinal translation of yoke (125) within oval-shaped slots (127A); and that pivoting of trigger (128) away from pistol grip (124) will cause distal longitudinal translation of yoke (125) within oval-shaped slots (127A).

A distal portion of yoke (125) is coupled with inner tube (134) of shaft assembly (130) via a coupling assembly (135). As discussed above, inner tube (134) is longitudinally translatable within outer sheath (132), such that inner tube (134) is configured to longitudinally translate concurrently with yoke (125). Furthermore, because pivoting of trigger (128) toward pistol grip (124) causes proximal longitudinal translation of yoke (125), it should be understood that pivoting of trigger (128) toward pistol grip (124) will cause proximal longitudinal translation of inner tube (134) relative to outer sheath (132) and handle assembly (120); and because pivoting of trigger (128) away from pistol grip (124) causes distal longitudinal translation of yoke (125), it should be understood that and that pivoting of trigger (128) away from pistol grip (124) will cause distal longitudinal translation of inner tube (134) relative to outer sheath (132) and handle assembly (120). Finally, because longitudinal translation of inner tube (134) causes rotation of clamp arm (144) toward and away from blade (160) as discussed above, it should be understood that pivoting of trigger (128) toward pistol grip (124) will cause clamp arm (144) to move toward ultrasonic blade (160); and that pivoting of trigger (128) away from pistol grip (124) will cause clamp arm (144) to move away from ultrasonic blade (160).

In some versions, one or more resilient members are used to bias clamp arm (144) and/or trigger (128) to the open position shown in FIG. 4. For instance, as shown in FIG. 5, a spring (136) is positioned within a proximal end of body (122) of the handle assembly (120). Spring (136) bears against body (122) and a proximal end of yoke (125) to thereby bias yoke (125) toward the distal position. Biasing of yoke (125) toward the distal position causes inner tube (134) to be biased distally and further causes trigger (128) to be biased away from pistol grip (124).

The foregoing components and operabilities of surgical instrument (100) are merely illustrative. Surgical instrument (100) may be configured in numerous other ways as will be apparent to those of ordinary skill in the art in view of the teachings herein. By way of example only, at least part of surgical instrument (100) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; and/or U.S. Pub. No. 2014/0114334, issued as U.S. Pat. No. 9,095,367 on Aug. 4, 2015. Additional merely illustrative variations for surgical instrument (100) will be described in greater detail below. It should be understood that the below described variations may be readily applied to surgical instrument (100) described above and any of the instruments referred to in any of the references that are cited herein, among others.

III. Multifunction Triggers for Ultrasonic Surgical Instrument

As discussed above, handle assembly (22, 120) may include control selector (30) and activation switch (32); where activation switch (32) may provide appropriate power to ultrasonic transducer (26, 112), and control selector (30) may allow the operator to select a desired power level or amplitude of ultrasonic energy. Alternatively, as also discussed above, handle assembly (22, 120) may include two or more activation switches (32) or buttons (126), each corresponding to different power levels or amplitudes of ultrasonic energy. Additionally, as discussed above, handle assembly (22, 120) may include a trigger (128) coupled to clamp arm (144) such that clamp arm (144) is pivotable towards ultrasonic blade (24, 160) to clamp tissue between clamp arm (144) and ultrasonic blade (24, 160).

In some instances, it may be desirable to incorporate the functionality of control selector (30), activation switch (32), or both control selector (30) and activation switch (32) into certain aspects of trigger (128). This may enable the operator to select a desired power level and/or activate ultrasonic blade (24, 160) by pivoting trigger (128) toward pistol grip (124). It should be understood that while the current examples are related to ultrasonic surgical instruments (20, 100), the principles of the current disclosure are not intended to be limited to ultrasonic surgical instruments (20, 100). One having ordinary skill in the art would immediately recognize these principles may be readily incorporated into a variety of different instruments requiring activation, power selection, and tissue manipulation. For example, the principles described herein may be incorporated into an RF surgical instrument or any other surgical instrument requiring electrical power.

A. Trigger with Mode Defining Closure

Figure 6A:
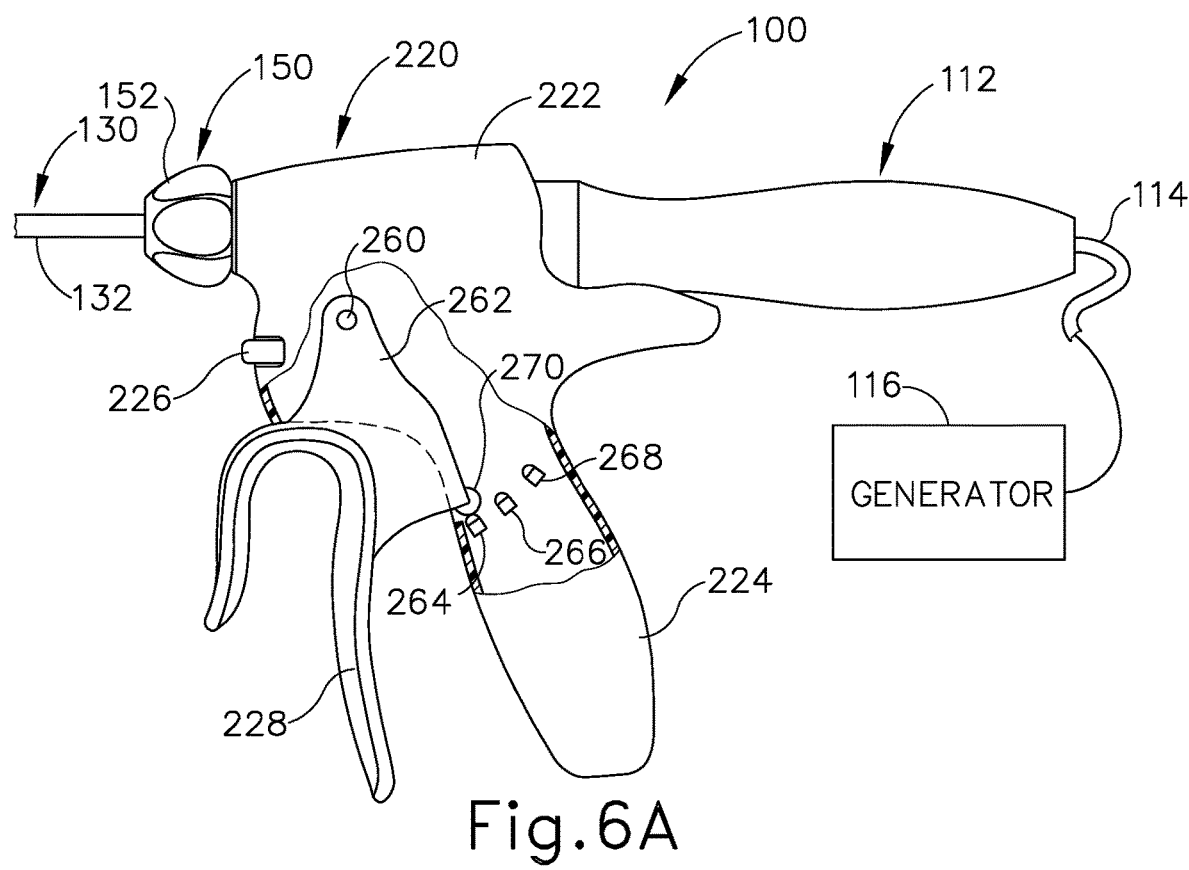
FIG. 6A depicts a side elevational view of another exemplary surgical instrument that may be incorporated into the system of FIG. 1, where the trigger is in a first position.
Figure 6B:
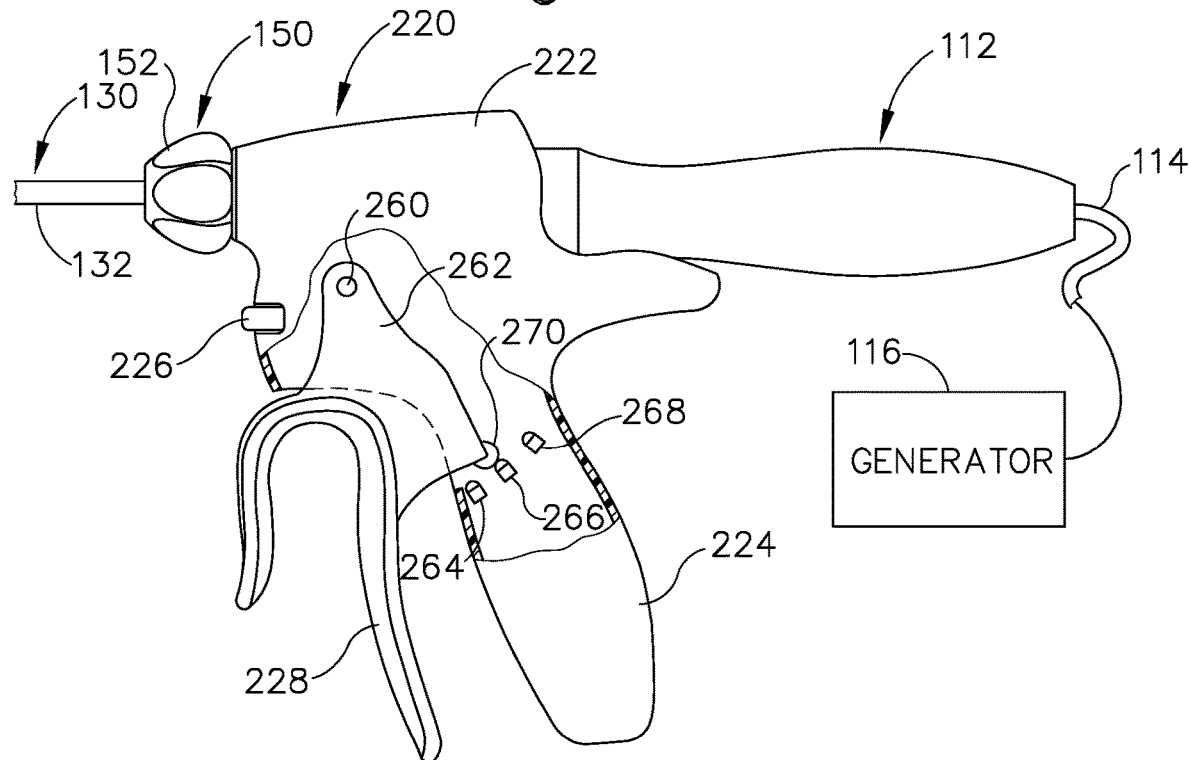
FIG. 6B depicts a side elevation view of the surgical instrument of FIG. 6A, where the trigger is in a second position.
Figure 6C:
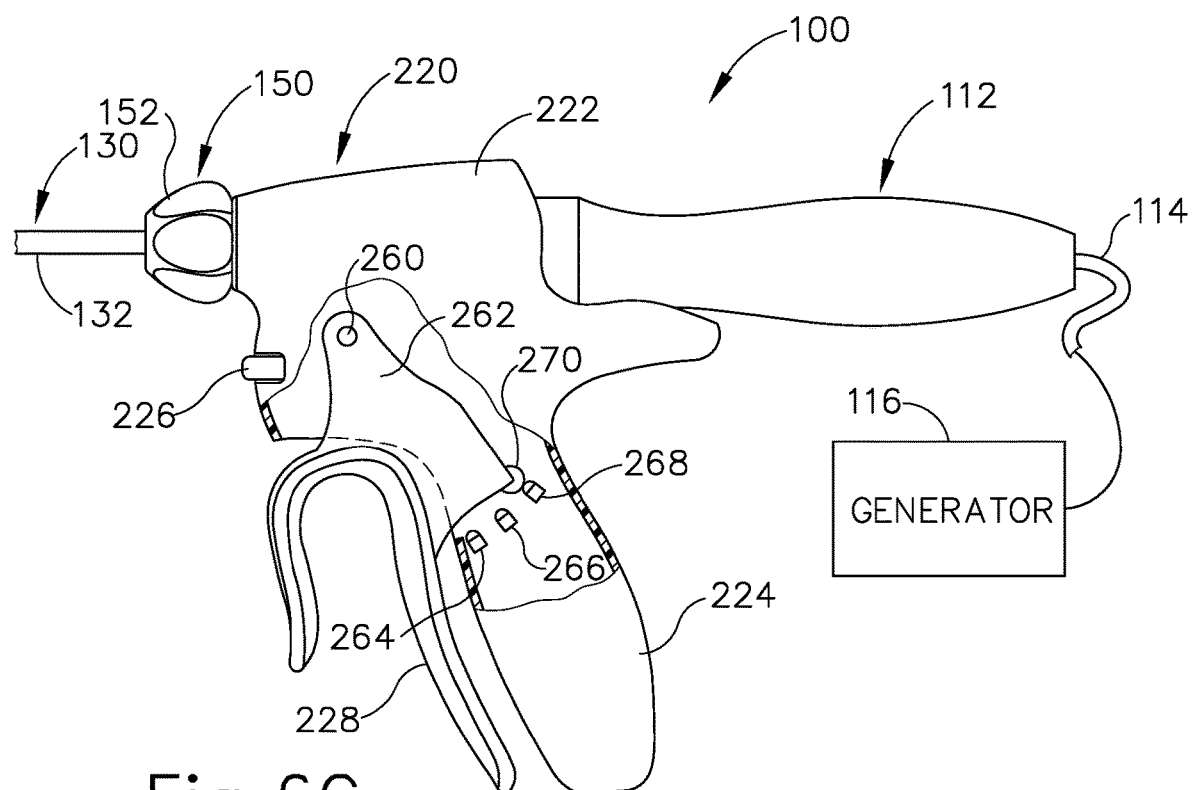
FIG. 6C depicts a side elevational view of the surgical instrument of FIG. 6A, where the trigger is in a third position.

1. Handle Assembly with Discrete, Trigger-Activated Power Level Selection Switches FIGS. 6A-6C show an alternative handle assembly (220) that may be incorporated into ultrasonic surgical instrument (100) described above. Like handle assembly (120), handle assembly (220) of this example includes a body (222), a pistol grip (224), and a trigger (228). These components are substantially similar to body (122), pistol grip (124), and trigger (128) described above, with the differences described below. Handle assembly (220) also receives an ultrasonic transducer (112), just like handle assembly (120) described above. It should be understood that clamp arm (144) may be coupled with trigger (228) such that clamp arm (144) is pivotable toward ultrasonic blade (160) in response to pivoting of trigger (228) toward pistol grip (224); and such that clamp arm (144) is pivotable away from ultrasonic blade (160) in response to pivoting of trigger (228) away from pistol grip (224). Various suitable ways in which clamp arm (144) may be coupled with trigger (228) will be apparent to those of ordinary skill in the art in view of the teachings herein. In some versions, one or more resilient members are used to bias clamp arm (144) and/or trigger (228) to the open position.

While handle assembly (120) includes two activation buttons (126), with one button (126) activating blade (160) at a low power and another button (126) activating blade (160) at a high power, handle assembly (220) of the present example includes only one activation button (226). In addition, pistol grip (224) houses three power switches (264, 266, 268). Trigger (228) includes a lever (262) that is pivotally coupled to body (222) via pin (260). A bridge (270) is unitarily fixed to lever (262).

As can be seen in FIGS. 6A-6C, bridge (270) is located on lever (262) such that as trigger (228) pivots towards pistol grip (224), bridge (270) successively contacts, and thereby activates, individual switches (264, 266, 268). Bridge (270) may only activate one individual switch (264, 266, 268) at time, corresponding to the pivotal location of trigger (228) relative to pistol grip (224). Individual switches (264, 266, 268) may be in electrical communication with circuit board (34). Activation of individual switches (264, 266, 268) via contact with bridge (270) will trigger a response in circuit board (34) that will select a specific corresponding power level or amplitude of ultrasonic energy to be delivered through blade (160). Thus, when button (226) is actuated while one of switches (264, 266, 268) is activated, transducer (112) will provide a corresponding power level or amplitude of ultrasonic energy to ultrasonic blade (160) based on a control signal from circuit board (34).

For example, when trigger (228) is in the position shown in FIG. 6A, bridge (270) activates switch (264). Activation of switch (264) may communicate with circuit board (34) to set the desired power level to low. Therefore, if the operator presses button (226) when trigger (228) is located at the position shown in FIG. 6A, ultrasonic blade (160) will activate to the corresponding low power level. Similarly, when trigger (228) is in the position shown in FIG. 6B, bridge (270) activates switch (266). Activation of switch (266) may communicate with circuit board (34) to set the desired power lever to medium. Therefore, if the operator presses button (226) when trigger (228) is located at the position shown in FIG. 6B, ultrasonic blade (160) will activate to the corresponding medium power level. Similarly, when trigger (228) is in the position shown in FIG. 6C, bridge (270) activates switch (268). Activation of switch (268) may communicate with circuit board (34) to set the desired power level to high. Therefore, if the operator presses button (226) when trigger (228) is located at the position shown in FIG. 6C, ultrasonic blade (160) will activate to the corresponding high power lever.

It should be understood that tactile feedback may be provided in order to indicate to the operator that trigger (228) has rotated from one power level to the next. For example, corresponding detents may be placed on pistol grip (224) and lever (262), where the detents are configured to interact with each other when trigger (228) rotates to and from the positions shown in FIGS. 6A-6C. Therefore, the operator will feel a click or sudden increase in physical resistance to further pivoting of trigger (228) when instrument (100) transitions from one power level to the next.

Optionally, if any one of switches (264, 266, 268) is not activated by contact with bridge (270), circuit board (34) may set the desired power level to off. Therefore, if the operator presses button (226) while bridge (270) is not in contact with any switch (264, 266, 268), ultrasonic blade (160) will remain inactivated. This may act as a safety switch. As another merely illustrative variation, trigger (228) may be modified such that one or more trigger switches are included on lever (262). Such trigger switches may be configured such that the trigger switch is positioned directly under button (226) when trigger (228) is pivoted to an appropriate position. In such versions, button (226) may be inoperable when a trigger switch is not positioned directly under button (226). In other words, the activation circuit may require closure of a trigger switch on lever (262) by button (226) in order for blade (160) to be activated. Such one or more trigger switches may be provided in addition to or in lieu of switches (264, 266, 268). In versions where one or more trigger switches are provided on lever (262) for engagement by button (226) and switches (264, 266, 268) are omitted, the different trigger switches may provide activation of blade (160) at different power levels and/or provide activation of end effector (140) at different power modalities.

While the power levels low, medium, and high are used in the foregoing example, one having ordinary skill in the art in view of the teachings herein would recognize these power levels are merely optional. For example, activation of any of the switches (264, 266, 268) may also communicate to circuit board (34) to set the desired power level to off. Therefore, contact between bridge (270) and any one of switches (264, 266, 268) may also act as a safety switch. Additionally, while three switches (264, 266, 268) are shown in the present example, any number of switches may be utilized as would be apparent to one having ordinary skill in the art in view of the teachings herein.

Trigger (228) may also be modified such that closure of clamp arm (144) relative to ultrasonic blade (160) occurs before bridge (270) makes contact with switch (264). In other words, switches (264, 266, 268) may be positioned such that trigger (228) can move through a first range of pivotal motion before contacting switch (264). Trigger (228) may thus at least partially pivot clamp arm (144) toward blade (160) during this first range of pivotal motion. In some such instances, trigger (228) is movable through a first range of motion to pivot clamp arm (144) toward blade (160) to a fully closed position; then trigger (228) is further pivotable through second, third, and fourth ranges of motion to enable bridge (270) to successively activate switches (264, 266, 268). During the second, third, and fourth ranges of motion of trigger (228), clamp arm (144) may provide progressively increasing compression of tissue against blade (160). Alternatively, a locking clutch may provide a coupling between clamp arm (144) and trigger (228), such that movement of trigger (228) through the second, third, and fourth ranges of motion do not have any effect on clamp arm (144). Various suitable ways in which this may be accomplished will be apparent to those of ordinary skill in the art in view of the teachings herein.

As noted above, bridge (270) of the present example is sized and configured such that bridge (270) will only activate one individual switch (264, 266, 268) at a time, based on the pivotal location of trigger (228) relative to pistol grip (224). In some other versions, however, bridge (270) may be sized and configured to activate more than one switch (264, 266, 268) at a time. For instance, in some alternative versions, bridge (270) is sized and configured to activate switch (264) after completing a first range of pivotal motion; to activate switches (264, 266) after completing a second range of pivotal motion; and to activate switches (264, 266, 268) after completing a third range of pivotal motion. The power level of ultrasonic blade (160) and/or other operational parameters may again vary based on activation of switches (264, 266, 268).

Figure 7A:
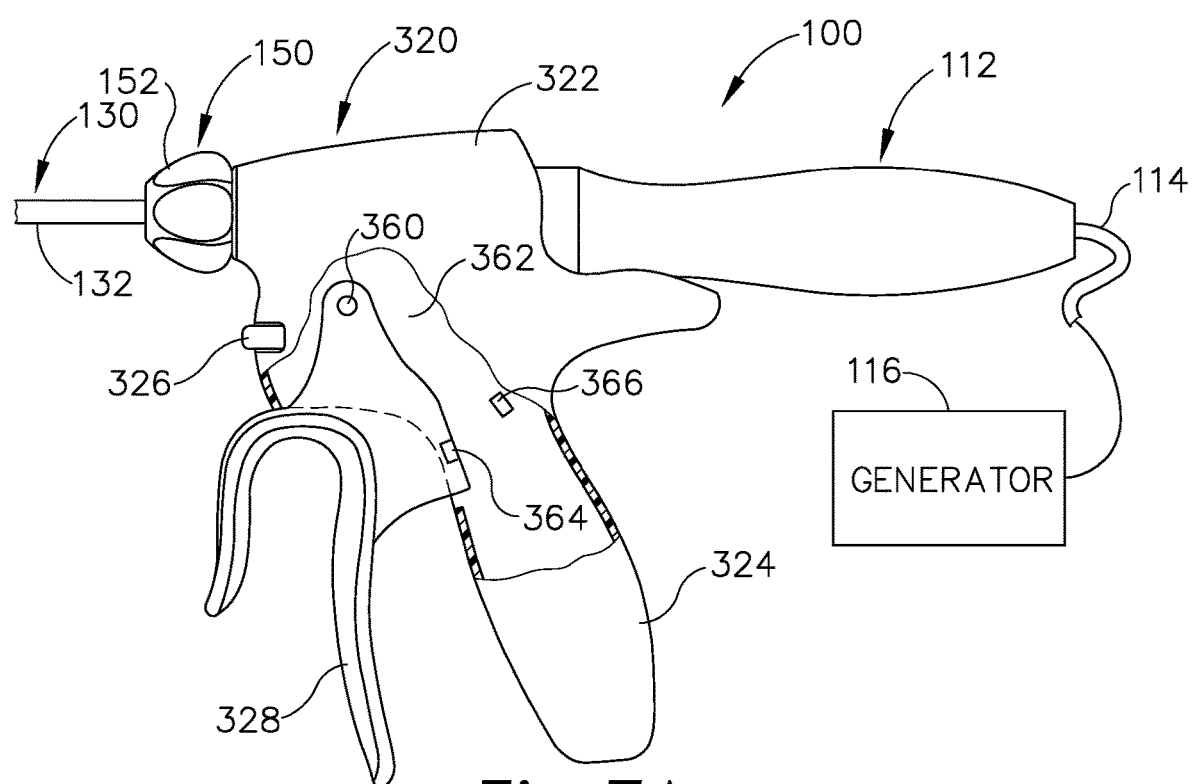
FIG. 7A depicts a side elevational view of another exemplary surgical instrument that may be incorporated into the system of FIG. 1, where the trigger is in a first position.
Figure 7B:
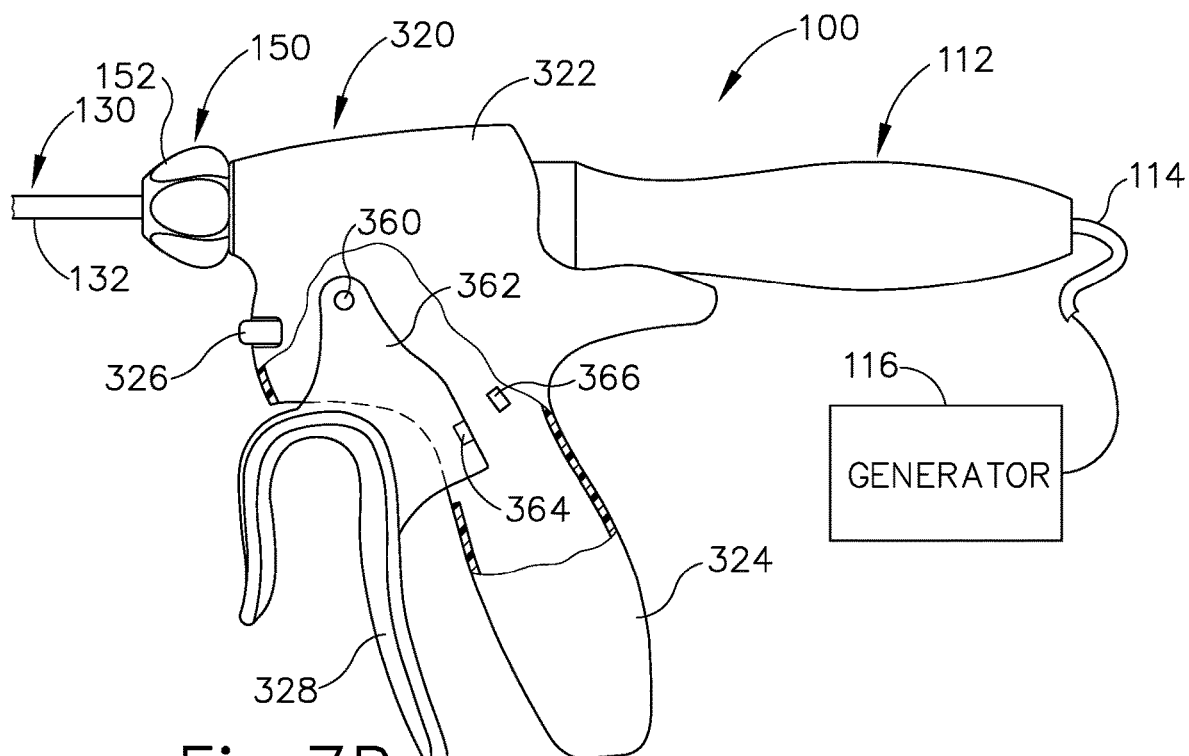
FIG. 7B depicts a side elevational view of the surgical instrument of FIG. 7A, where the trigger is in a second position.
Figure 7C:
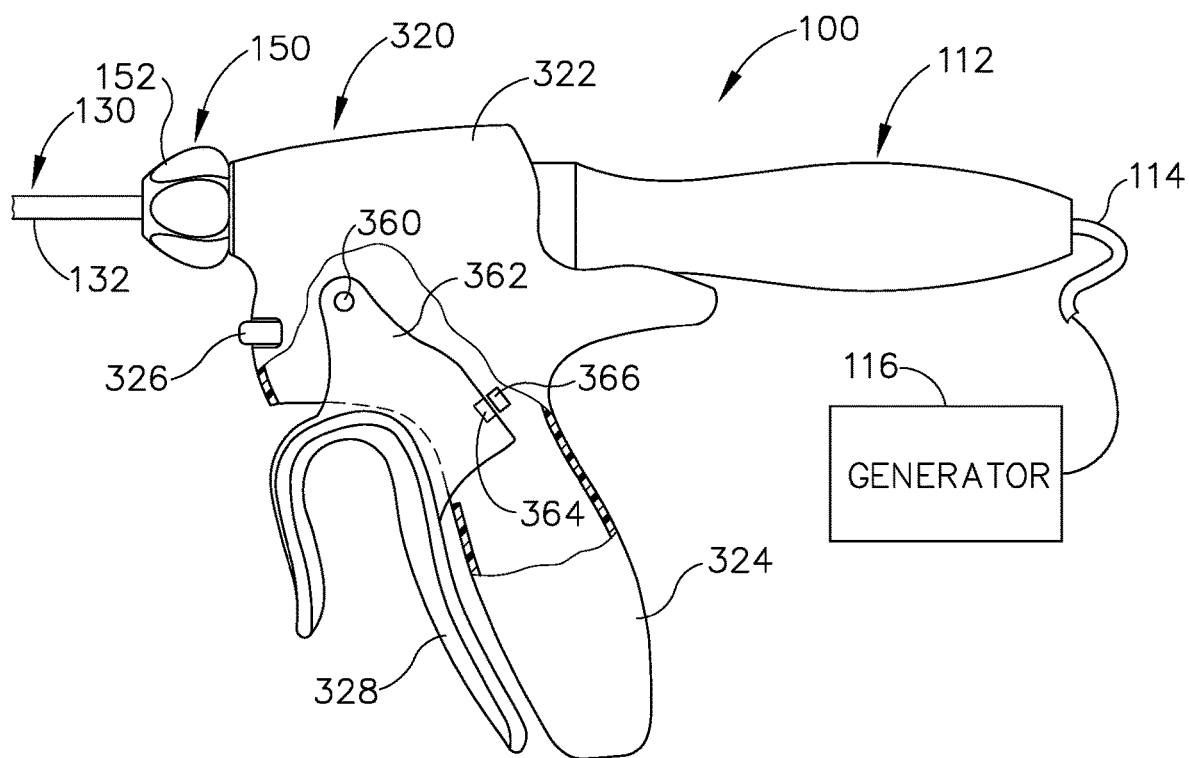
FIG. 7C depicts a side elevational view of the surgical instrument of FIG. 7A, where the trigger is in a third position.

2. Handle Assembly with Hall Effect Sensor to Detect Trigger Position and Select Ultrasonic Power Level FIGS. 7A-7C show an alternative handle assembly (320) that may be incorporated into ultrasonic surgical instrument (100) described above. Like handle assembly (120), handle assembly (320) of this example includes a body (322), a pistol grip (324), and a trigger (328). These components are substantially similar to body (122), pistol grip (124), and trigger (128) described above, with the differences described below. Handle assembly (320) also receives an ultrasonic transducer (112), just like handle assembly (120) described above. It should be understood that clamp arm (144) may be coupled with trigger (328) such that clamp arm (144) is pivotable toward ultrasonic blade (160) in response to pivoting of trigger (328) toward pistol grip (324); and such that clamp arm (144) is pivotable away from ultrasonic blade (160) in response to pivoting of trigger (328) away from pistol grip (324). Various suitable ways in which clamp arm (144) may be coupled with trigger (328) will be apparent to those of ordinary skill in the art in view of the teachings herein. In some versions, one or more resilient members are used to bias clamp arm (144) and/or trigger (328) to the open position.

While handle assembly (120) includes two activation buttons (126), with one button (126) activating blade (160) at a low power and another button (126) activating blade (160) at a high power, handle assembly (320) of the present example includes only one activation button (326). In addition, pistol grip (324) of the present example houses a Hall Effect sensor (366). Trigger (328) includes a lever (362) that is pivotally coupled to body (322) via pin (360). A magnet (364) is unitarily fixed to lever (362).

As can be seen in FIGS. 7A-7C, magnet (364) is located on lever (362) such that as trigger (328) pivots toward pistol grip (224), magnet (364) rotates closer to Hall Effect sensor (366). As magnet (364) rotates closer to Hall Effect sensor (366), sensor (366) varies its output voltage. Hall Effect sensor (366) is in electrical communication with circuit board (34). Hall Effect sensor (366) thereby communicates an output voltage to circuit board (34) based in part on the distance between magnet (364) and Hall Effect sensor (366). Circuit board (34) is configured to select a specific power level or amplitude of ultrasonic energy based on a range of voltages received from Hall Effect sensor (366). Thus, when button (326) is activated while magnet (364) is within a predetermined distance of Hall Effect sensor (366), transducer (112) will provide a corresponding power level or amplitude of ultrasonic energy to ultrasonic blade (160) based on a control signal from circuit board (34).

For example, when trigger (328) is in the position shown in FIG. 7A, magnet (364) is at a first distance relative to Hall Effect sensor (366). Therefore, Hall Effect sensor (366) outputs a corresponding voltage to circuit board (34). The voltage corresponding to position of trigger (328) shown in FIG. 7A may signal to circuit board (34) to set the desired power level to low. Therefore, if the operator presses button (326) when trigger (328) is located at the position shown in FIG. 7A, ultrasonic blade (160) will activate to the corresponding low power level.

Similarly, when trigger (328) is in the position shown in FIG. 7B, magnet (364) is at a second, closer distance relative to Hall Effect sensor (366). Therefore, Hall Effect sensor (366) outputs a corresponding voltage to circuit board (34). The voltage corresponding to position of trigger (328) shown in FIG. 7B may signal to circuit board (34) to set the desired power level to medium. Therefore, if the operator presses button (326) when trigger (328) is located at the position shown in FIG. 7B, ultrasonic blade (160) will activate to the corresponding medium power level.

Similarly, when trigger (328) is in the position shown in FIG. 7C, magnet (364) is at a third, closest distance relative to Hall Effect sensor (366). Therefore, Hall Effect sensor (366) outputs a corresponding voltage to circuit board (34). The voltage corresponding to position of trigger (328) shown in FIG. 7C may signal to circuit board (34) to set the desired power level to high. Therefore, if the operator presses button (326) when trigger (328) is located at the position shown in FIG. 7C, ultrasonic blade (160) will activate to the corresponding high power level.

It should be understood that tactile feedback may be provided in order to indicate to the operator that trigger (328) has rotated from one power level to the next. For example, corresponding detents may be placed on pistol grip (324) and lever (362), where the detents are configured to interact with each other when trigger (328) rotates to and from the positions shown in FIGS. 7A-7C. Therefore, the operator will feel a click or sudden increase in physical resistance to further pivoting of trigger (328) when instrument (100) transitions from one power level to the next.

While the power levels low, medium, and high are used, one having ordinary skill in the art in view of the teachings herein would recognize these power levels are merely optional. For example, a location of any distance between magnet (364) and Hall Effect sensor (366) may provide a corresponding output voltage that signals to circuit board (34) to set the desired power level to off. Therefore, if the operator presses button (326) while the corresponding output voltage sets the desired power level to off, ultrasonic blade (160) will remain inactive. This may effectively act as a safety switch.

Additionally, while three distances are shown in the present example, any number of distances with corresponding power levels may be utilized as would be apparent to one having ordinary skill in the art in view of the teachings herein. Moreover, the ultrasonic power level may be continuously variable along a range of power, such that the available levels need not necessarily be limited to a specific, discrete number of power levels. In other words, the ultrasonic power level may have some proportional relationship with the pivotal position of trigger (328), since Hall Effect sensor (366) is capable of generating continuously variable output voltages along a range based on the proximity of magnet (364) to Hall Effect sensor (366).

Circuit board (34) and/or Hall Effect sensor (366) may also be configured such that trigger (328) is movable through a first range of motion to at least partially pivot clamp arm (144) toward blade (160) without providing a selection of an ultrasonic power level. For instance, Hall Effect sensor (366) may be configured such that Hall Effect sensor (366) does not sense the magnetic field of magnet (364) and therefore does not generate a voltage until trigger (328) has moved through the first range of motion. In addition or in the alternative, circuit board (34) may be configured to be essentially non-responsive to voltages from Hall Effect sensor (366) that fall below a threshold level that is associated with trigger (328) completing a first range of motion.

While a Hall Effect sensor (366) is used in the present example to provide contact-less sensing of proximity, it should be understood that other kinds of components may be used to sense the proximity of a portion of trigger (328) without having to contact trigger (328). By way of example only, magnet (364) may be omitted and Hall Effect sensor (366) may be replaced with a conventional proximity sensor, including but not limited to a capacitive sensor, an inductive sensor, a photocell, etc. Other suitable variations will be apparent to those of ordinary skill in the art in view of the teachings herein.

Figure 8A:
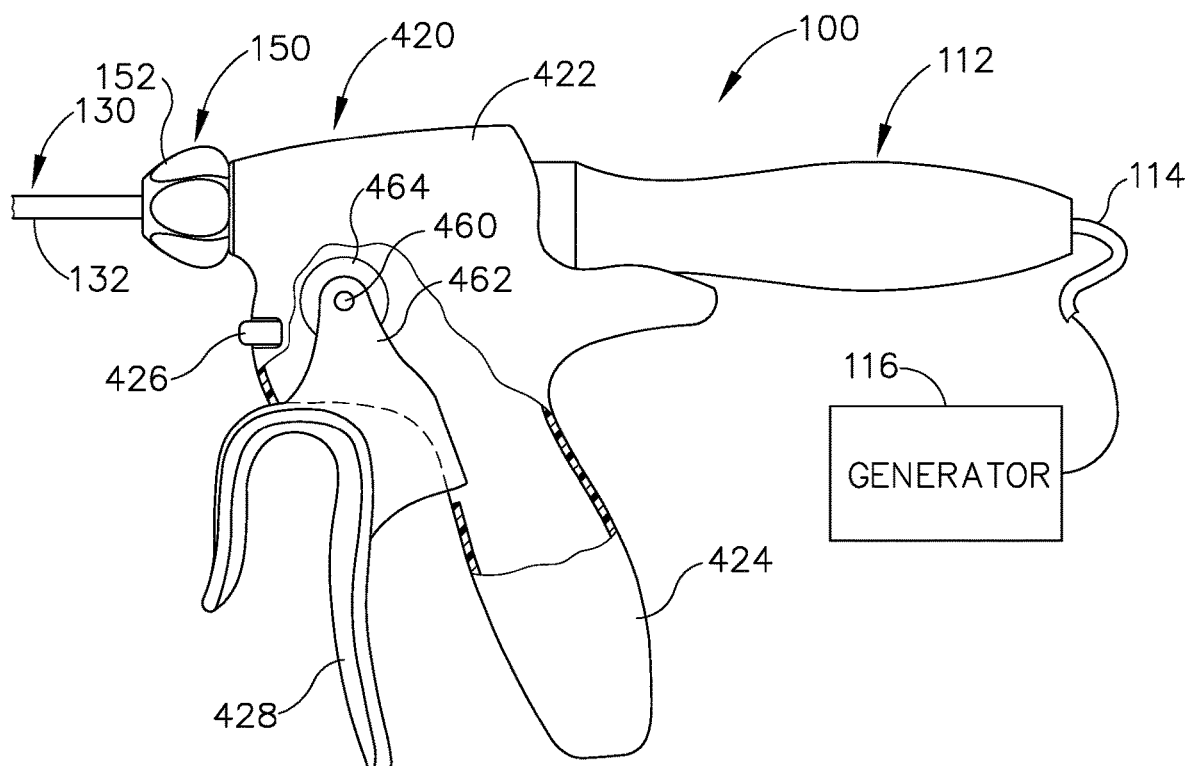
FIG. 8A depicts a side elevational view of another exemplary surgical instrument that may be incorporated into the system of FIG. 1, where the trigger is in a first position.
Figure 8B:
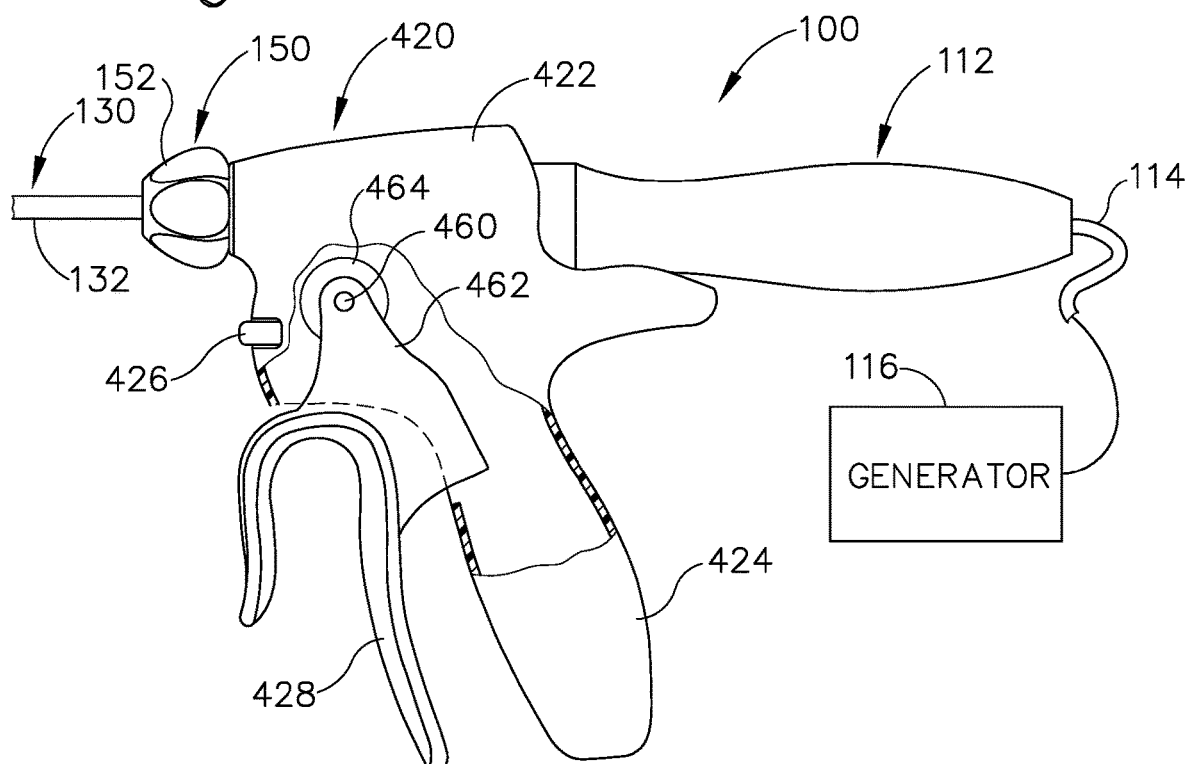
FIG. 8B depicts a side elevational view of the surgical instrument of FIG. 8A, where the trigger is in a second position.
Figure 8C:
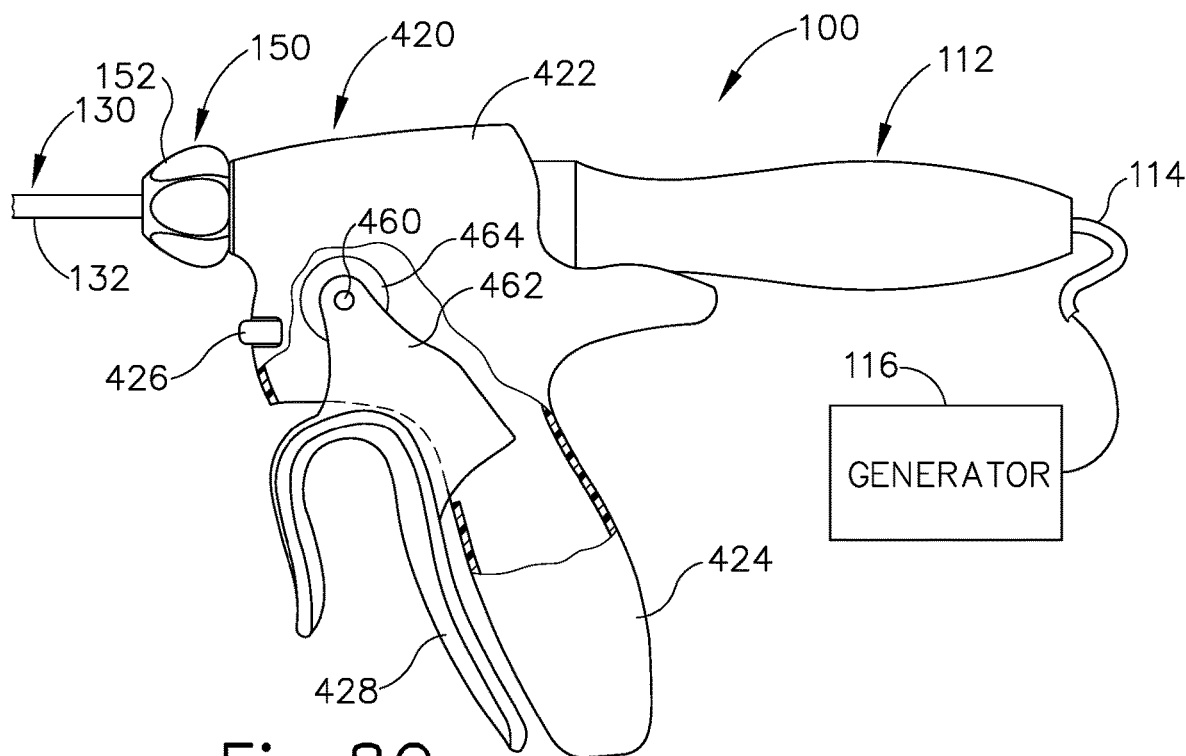
FIG. 8C depicts a side elevational view of the surgical instrument of FIG. 8A, where the trigger is in a third position.

3. Handle Assembly with Force Transducer to Detect Trigger Position and Select Ultrasonic Power Level FIGS. 8A-8C show an alternative handle assembly (420) that may be incorporated into ultrasonic surgical instrument (100) described above. Like handle assembly (120), handle assembly (420) of this example includes a body (422), a pistol grip (424), and a trigger (428). These components are substantially similar to body (122), pistol grip (124), and trigger (128) described above, with the differences described below. Handle assembly (420) also receives an ultrasonic transducer (112), just like handle assembly (120) described above. It should be understood that clamp arm (144) may be coupled with trigger (428) such that clamp arm (144) is pivotable toward ultrasonic blade (160) in response to pivoting of trigger (428) toward pistol grip (424); and such that clamp arm (144) is pivotable away from ultrasonic blade (160) in response to pivoting of trigger (428) away from pistol grip (424). Various suitable ways in which clamp arm (144) may be coupled with trigger (428) will be apparent to those of ordinary skill in the art in view of the teachings herein. In some versions, one or more resilient members are used to bias clamp arm (144) and/or trigger (428) to the open position.

While handle assembly (120) includes two activation buttons (126), with one button (126) activating blade (160) at a low power and another button (126) activating blade (160) at a high power, handle assembly (420) of the present example includes only one activation button (426). Trigger (428) of the present example includes a lever (462) that is pivotally coupled to body (422) via pin (460); and a spring loaded torque transducer (464) associated with lever (362). Spring loaded torque transducer (464) is configured to resiliently bias trigger (428) and lever (462) to an open or distal position relative to pistol grip (424). Spring loaded torque transducer (464) is in electrical communication with circuit board (34). As trigger (428) rotates toward pistol grip (424), as shown in FIGS. 8A-8C, spring loaded torque transducer (464) imparts a measurable force on trigger (428) in an attempt to bias trigger (428) back into the open position. Spring loaded torque transducer (464) generates a progressively increasing force on trigger (428) the farther trigger (428) is displaced from the open position.

Spring loaded torque transducer (464) also generates an electrical output corresponding to the measurable force imparted on trigger (428) and sends this electrical output to circuit board (34). Circuit board (34) may then use the output to select a predetermined power level. Thus, when button (426) is activated while spring loaded torque transducer (464) sends a measurable output to circuit board (34) indicating a specific power level, transducer (112) will provide a corresponding power level or amplitude of ultrasonic energy to ultrasonic blade (160) based on a control signal from circuit board (34).

For example, when trigger (428) is in the position shown in FIG. 8A, spring loaded torque transducer (464) imparts a first measurable force on trigger (428). Therefore, spring loaded torque transducer (464) outputs a corresponding electrical output to circuit board (34). The voltage corresponding to the force generated by spring loaded torque transducer (464) based on the position of trigger (428) shown in FIG. 8A may signal to circuit board (34) to set the desired power level to low. Therefore, if the operator presses button (426) when trigger (428) is located at the position shown in FIG. 8A, ultrasonic blade (160) will activate to the corresponding low power level.

Similarly, when trigger (428) is in the position shown in FIG. 8B, spring loaded torque transducer (464) imparts a second, greater measurable force on trigger (428). Therefore, spring loaded torque transducer (464) outputs a corresponding electrical output to circuit board (34). The voltage corresponding to the force generated by spring loaded torque transducer (464) based on the position of trigger (428) shown in FIG. 8B may signal to circuit board (34) to set the desired power level to medium. Therefore, if the operator presses button (426) when trigger (428) is located at the position shown in FIG. 8B, ultrasonic blade (160) will activate to the corresponding medium power level.

Similarly, when trigger (428) is in the position shown in FIG. 8C, spring loaded torque transducer (464) imparts a third, greatest measurable force on trigger (428). Therefore, spring loaded torque transducer (464) outputs a corresponding electrical output to circuit board (34). The voltage corresponding to the force generated by spring loaded torque transducer (464) based on the position of trigger (428) shown in FIG. 8C may signal to circuit board (34) to set the desired power level to high. Therefore, if the operator presses button (426) when trigger (428) is located at the position shown in FIG. 8C, ultrasonic blade (160) will activate to the corresponding high power level.

It should be understood that tactile feedback may be provided in order to indicate to the operator that trigger (428) has rotated from one power level to the next. For example, corresponding detents may be placed on pistol grip (424) and lever (462), where the detents are configured to interact with each other when trigger (428) rotates to and from the positions shown in FIGS. 8A-8C. Therefore, the operator will feel a click or sudden increase in physical resistance to further pivoting of trigger (428) when instrument (100) transitions from one power level to the next.

While the power levels low, medium, and high are used, one having ordinary skill in the art in view of the teachings herein would recognize these power levels are merely optional. For example, a force imparted on trigger (428) by spring loaded torque transducer (464) may provide a corresponding output voltage that signals to circuit board (34) to set the desired power level to off. Therefore, if the operator presses button (426) while the corresponding output voltage sets the desired power level to off, ultrasonic blade (160) will remain inactive. This may effectively act as a safety switch.

Additionally, while three distances are shown in the present example, any number of distances with corresponding power levels may be utilized as would be apparent to one having ordinary skill in the art in view of the teachings herein. Moreover, the ultrasonic power level may be continuously variable along a range of power, such that the available levels need not necessarily be limited to a specific, discrete number of power levels. In other words, the ultrasonic power level may have some proportional relationship with the pivotal position of trigger (428), since torque transducer (464) is capable of generating continuously variable output voltages along a range based on the resistance force imposed on trigger (428) by torque transducer (464).

Circuit board (34) and/or torque transducer (464) may also be configured such that trigger (428) is movable through a first range of motion to at least partially pivot clamp arm (144) toward blade (160) without providing a selection of an ultrasonic power level. For instance, torque transducer (464) may be configured such that torque transducer (464) does not generate a voltage until trigger (428) has moved through the first range of motion. In addition or in the alternative, circuit board (34) may be configured to be essentially non-responsive to voltages from torque transducer (464) that fall below a threshold level that is associated with trigger (428) completing a first range of motion.

It should be understood that torque transducer (464) may be replaced with a variety of other components. By way of example only, a rotary encoder, rotary potentiometer, rheostat, or other device that is capable of indicating the pivotal position of trigger (428) may be used in place of torque transducer (464). Other suitable substitutes will be apparent to those of ordinary skill in the art in view of the teachings herein.

While handle assembly (420) provides three discrete power levels in the present example, it should be understood that torque transducer (464) (or any substitute therefor) may be used to provide continuous feedback on the pivotal position of trigger (428), and this feedback may be used to provide a continuously variable power level for blade (160). In other words, the power level may change linearly or otherwise proportionally based on the pivotal position of trigger (428). Alternatively, circuit board (34) may still provide a stepped response that mimics discrete switches to provide discrete power levels in response to continuous feedback on the pivotal position of trigger (428).

B. Handle Assembly with Movable Trigger Actuated Buttons to Select Power Level

FIGS. 9A-11 show an alternative handle assembly (520) that may be incorporated into ultrasonic surgical instrument (100) described above. Like handle assembly (120), handle assembly (520) of this example includes a body (522), a pistol grip (524), and a trigger (528). These components are substantially similar to body (122), pistol grip (124), and trigger (128) described above, with the differences described below. Handle assembly (520) also receives an ultrasonic transducer (112), just like handle assembly (120) described above. It should be understood that clamp arm (144) may be coupled with trigger (528) such that clamp arm (144) is pivotable toward ultrasonic blade (160) in response to pivoting of trigger (528) toward pistol grip (524); and such that clamp arm (144) is pivotable away from ultrasonic blade (160) in response to pivoting of trigger (528) away from pistol grip (524). Various suitable ways in which clamp arm (144) may be coupled with trigger (528) will be apparent to those of ordinary skill in the art in view of the teachings herein. In some versions, one or more resilient members are used to bias clamp arm (144) and/or trigger (528) to the open position.

While handle assembly (120) includes two activation buttons (126), with one button (126) activating blade (160) at a low power and another button (126) activating blade (160) at a high power, handle assembly (520) of the present example includes only one activation button (526). In addition, pistol grip (524) of the present example includes a plurality of slots (570). A button (572) is rotatably disposed in each slot (572). As will be described in greater detail below, rotatable buttons (572) are capable of rotating from an "activated" position to a "deactivated" position, which in turn may change the functionality of pressing activation button (526). Additionally, trigger (528) further includes a lever (562) extending distally from trigger (528); and a finger grip (560) extending from lever (562).

Figure 9A:
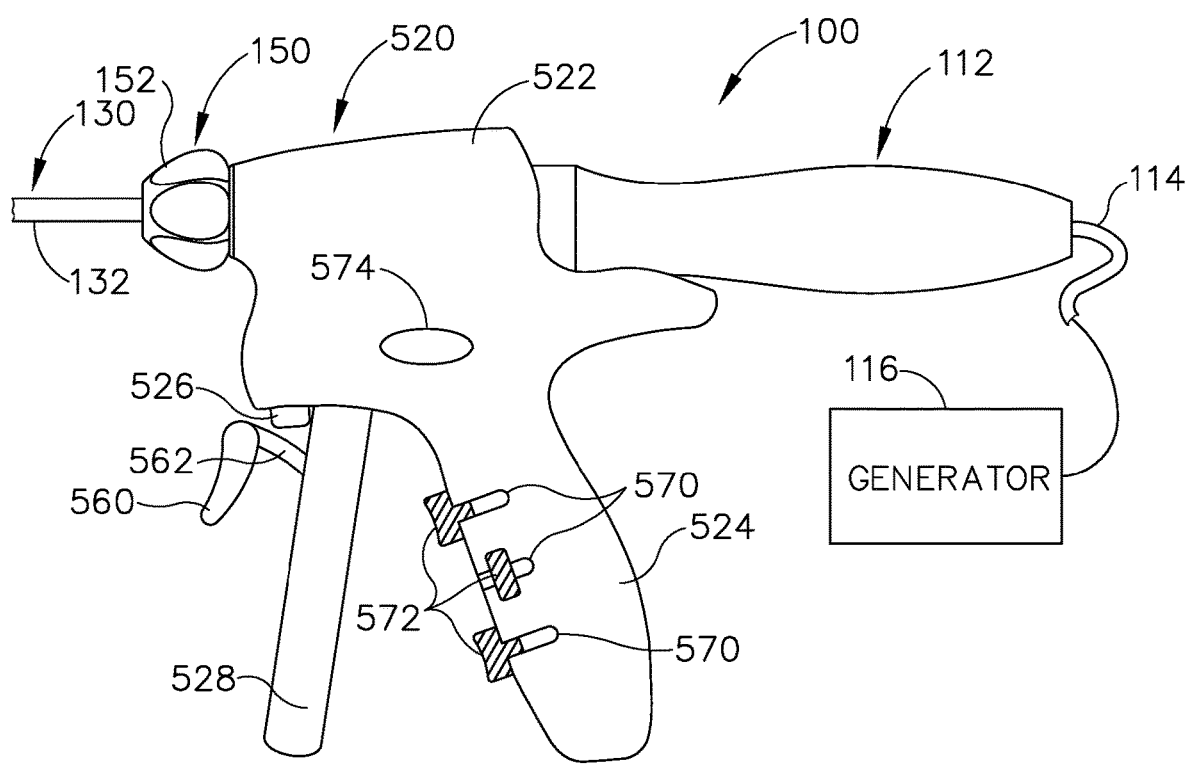
FIG. 9A depicts a side elevational view of another exemplary surgical instrument that may be incorporated into the system of FIG. 1, where in trigger is in a first position and the movable buttons are in a first configuration.
Figure 9B:
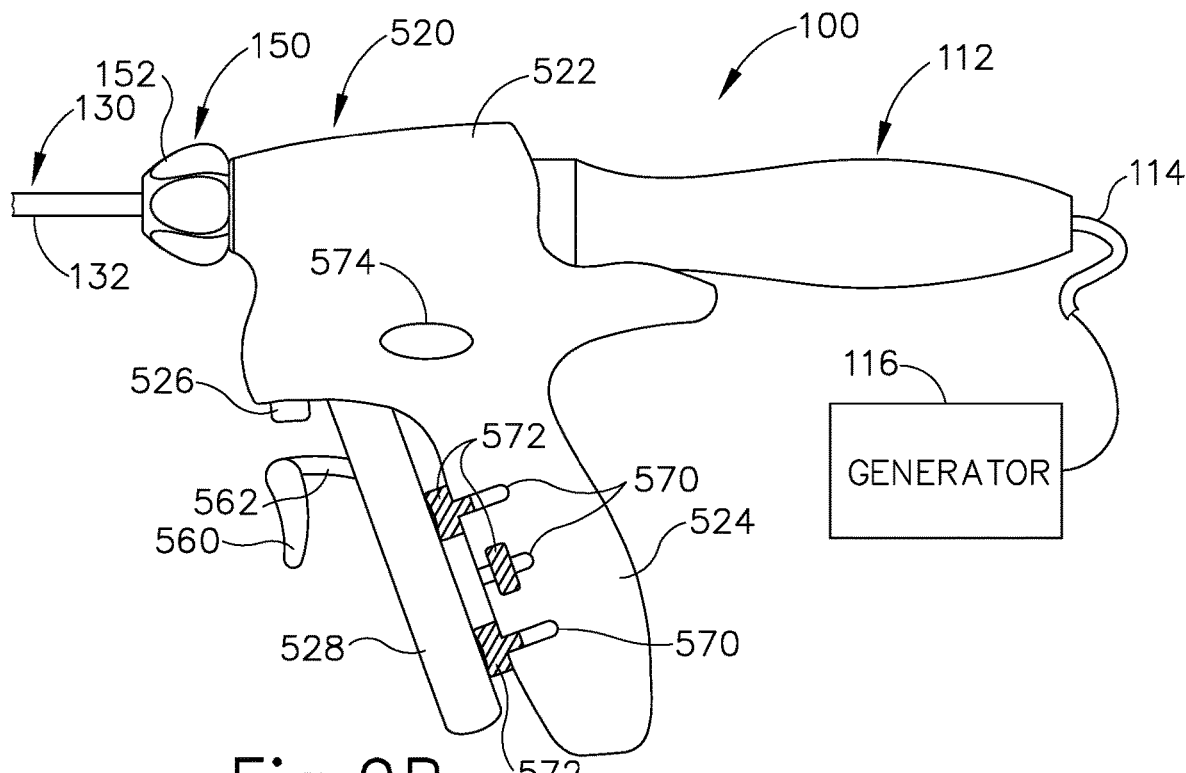
FIG. 9B depicts a side elevational view of the surgical instrument of FIG. 9A, where the trigger is in a second position and the movable buttons are in the first configuration.
Figure 9C:
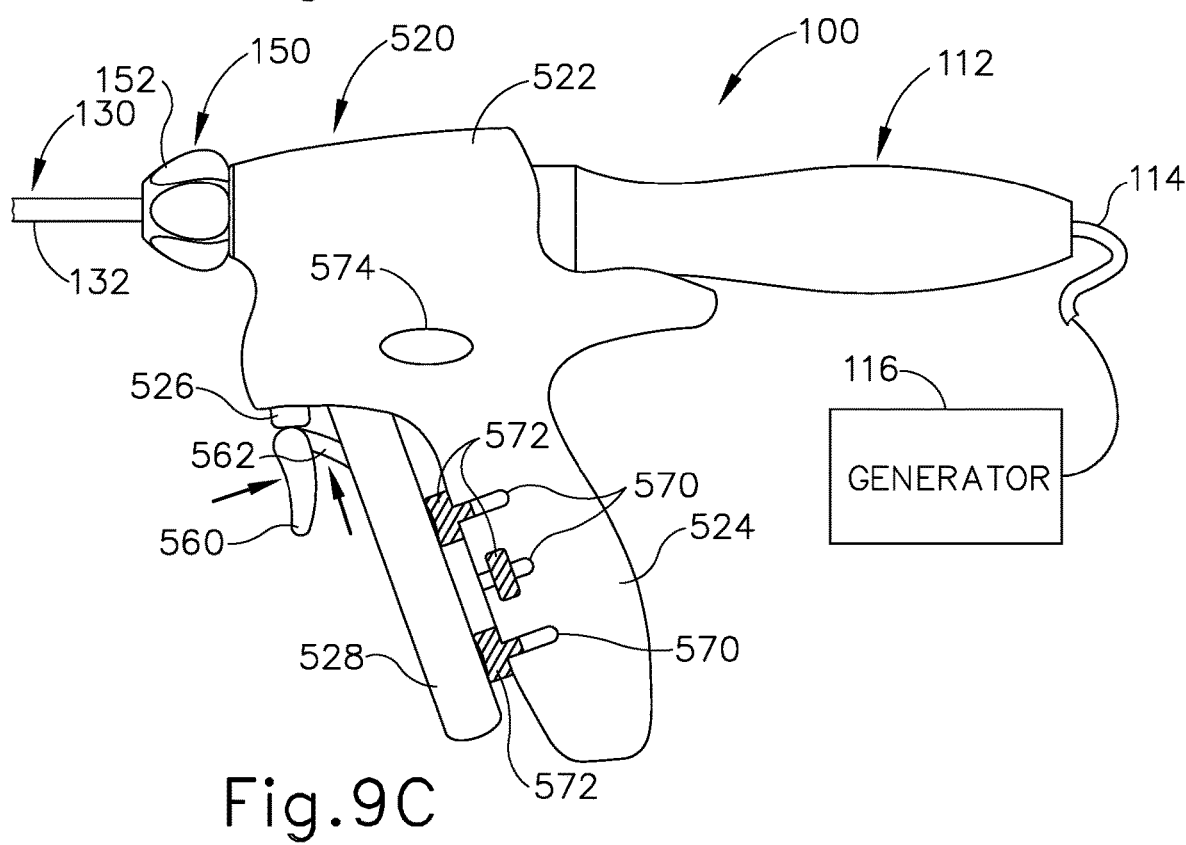
FIG. 9C depicts a side elevational view of the surgical instrument of FIG. 9A, where the trigger is in a third position and the movable buttons are in the first configuration.
Figure 10:
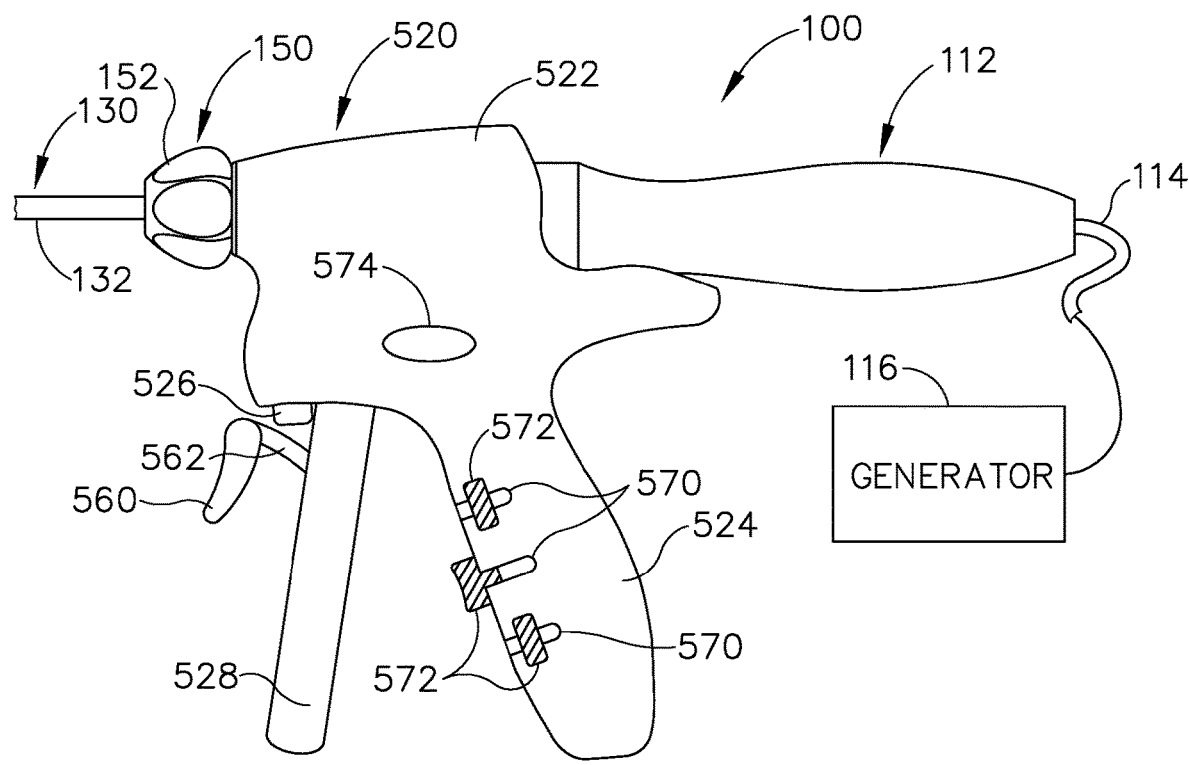
FIG. 10 depicts a side elevational view of the surgical instrument of FIG. 9A, where the trigger is in the first position and the movable buttons are in a second configuration.
Figure 11:
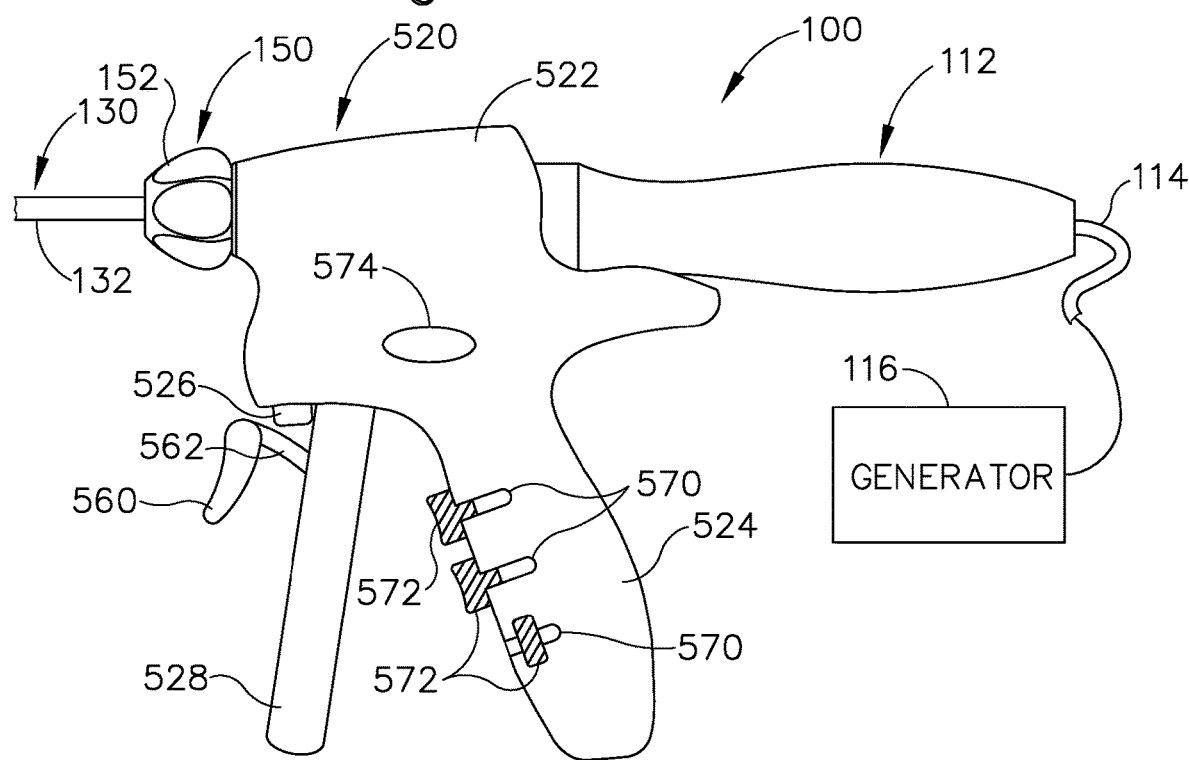
FIG. 11 depicts a side elevational view of the surgical instrument of FIG. 9A, where the trigger is in the first position and the movable buttons are in a third configuration.

FIGS. 9A-9C show an exemplary use of handle assembly (520) incorporated into instrument (100). As shown in FIG. 9A, trigger (528) is in an open position relative to pistol grip (524). Therefore, as described above, clamp arm (144) is pivoted away from ultrasonic blade (160). It should be understood that the top and bottom rotatable buttons (572) are rotated within slots (570) of pistol grip (524) to face towards trigger (528) in such a way as to make contact with the face of trigger (528) when trigger (528) is fully pivoted toward pistol grip (524). Therefore, the top and bottom rotatable buttons (572) are in the distally projecting, "activated" position. The middle rotatable button (572) is rotated within slot (570) of pistol grip (524) to face away from trigger (528) in such a way as to not make contact with the face of trigger (528) when trigger (528) is fully pivoted toward pistol grip (524). Therefore the middle rotatable button (572) is in the laterally projecting, "deactivated" position. It should be understood that, as shown in FIGS. 10-11, any number of combinations of rotatable buttons (572) can be switched to the "activated" and "deactivated" positions.

FIG. 9B shows trigger (528) pivoted to toward pistol grip (524) to the closed position. A proximal face of trigger (528) makes contact with the top and bottom rotatable buttons (572) without making contact with the middle rotatable button (572). Rotatable buttons (572) are in electrical communication with circuit board (34). Thus, when rotatable buttons (572) are in the "activated" position, rotatable buttons (572) send a message to circuit board (34) when the face of trigger (528) makes contact with rotatable buttons (572). Each rotatable button (572) that is in the "activated" position and in contact with trigger (528) may be configured to signal to circuit board (34) to activate or deactivate certain features or modes of operations. Additionally or alternatively, a combination of rotatable buttons (572) in the "activated" position and in contact with trigger (528) may be configured to signal to circuit board (34) to activate or deactivate certain features or modes of operation. Optionally, circuit board (34) may also be configured to only deactivate certain feature and/or modes of operation when a specific rotatable button (572) or combinations of rotatable buttons (572) are in the "activated" position and in contact with trigger (528). Other functionalities of rotatable buttons (572) being activated or deactivated will be apparent to one having ordinary skill in the art in view of the teachings herein.

For example, a specific individual rotatable button (572) or combination of rotatable buttons (572) being rotated into the "activated" position may signal to circuit board (34), when trigger (528) is rotated toward pistol grip (524), to activate a "cool blade after transection" feature. This feature may provide cooling of ultrasonic blade (160) after end effector (140) has been used to transect tissue. Alternatively, a specific individual rotatable button (572) or combination of rotatable buttons (572) rotated into the activated position may signal to circuit board (34), when trigger (528) is rotated toward pistol grip (524), to activate a feature that leaves blade (160) hot after a transection. Another specific individual rotatable button (572) or combination of rotatable buttons (572) rotated into the activated position may signal to circuit board (34), when trigger (528) is rotated toward pistol grip (524), to activate a low power setting or a high power setting.

As shown in FIG. 9C, once trigger (528) has been pivoted to a closed position relative to pistol grip (524), the operator may actuate finger grip (560) toward trigger (528), causing lever (562) to rotate or deflect upwardly to make contact with activation button (526). Activation button (526) will activate ultrasonic blade (160), while the contact between trigger (528) and rotatable buttons (572) in the "activated" position determines the features and/or modes of operation at which the ultrasonic blade (160) is activated.

Lever (562) may be rotatably coupled to trigger (528) such that actuation of finger grip (560) toward trigger (528) causes lever (562) to rotate upwardly to make contact with activation button (526). Lever (562) may also be biased to the positions shown in FIGS. 9A-9B, such that once the operator releases compression force off finger grip (560), lever (562) returns to the positions shown in FIGS. 9A-9B. Any other suitable methods in which lever (562) and finger grip (560) activate button (526) will be apparent to one having ordinary skill in the art in view of the teachings herein. Alternatively, button (526) may be placed on other locations of body (522) that obviates the need to have lever (526) and finger grip (560), such as the locations where button (126, 226, 326, 426) is in relation to body (122, 222, 322, 422) described above.

Handle assembly (520) of the present example further includes an RF activation button (574). This button (574) is operable to provide the delivery of RF electrosurgical energy to tissue via end effector (140). To that end, end effector (140) may be modified to be configured and operable in accordance with at least some of the teachings of U.S. Pat. No. 8,663,220, entitled "Ultrasonic Electrosurgical Instruments," issued Mar. 4, 2014, the disclosure of which is incorporated by reference herein. In addition or in the alternative, button (574) may be configured and operable in accordance with at least some of the teachings of U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein. It should be understood that button (574) may be readily incorporated into any of the various other handle assemblies describe herein. It should also be understood that button (574) may simply be omitted from handle assembly (574), if desired.

As another merely illustrative variation, the proximal face of trigger (528) may have one or more discrete buttons that are engaged by whichever rotatable button(s) (572) is/are rotated to the activated position when trigger (528) is pivoted toward pistol grip (524). In some such versions, these buttons on trigger (528) are actuated simultaneously with whichever rotatable button(s) (572) is/are rotated to the activated position when trigger (528) is pivoted toward pistol grip (524). In some other versions, rotatable buttons (572) are simply passive stops that activate the buttons on trigger (528), such that rotatable buttons (572) are not capable of themselves being actuated.

C. Activation Button with Integrated Damping System

Figure 12A:
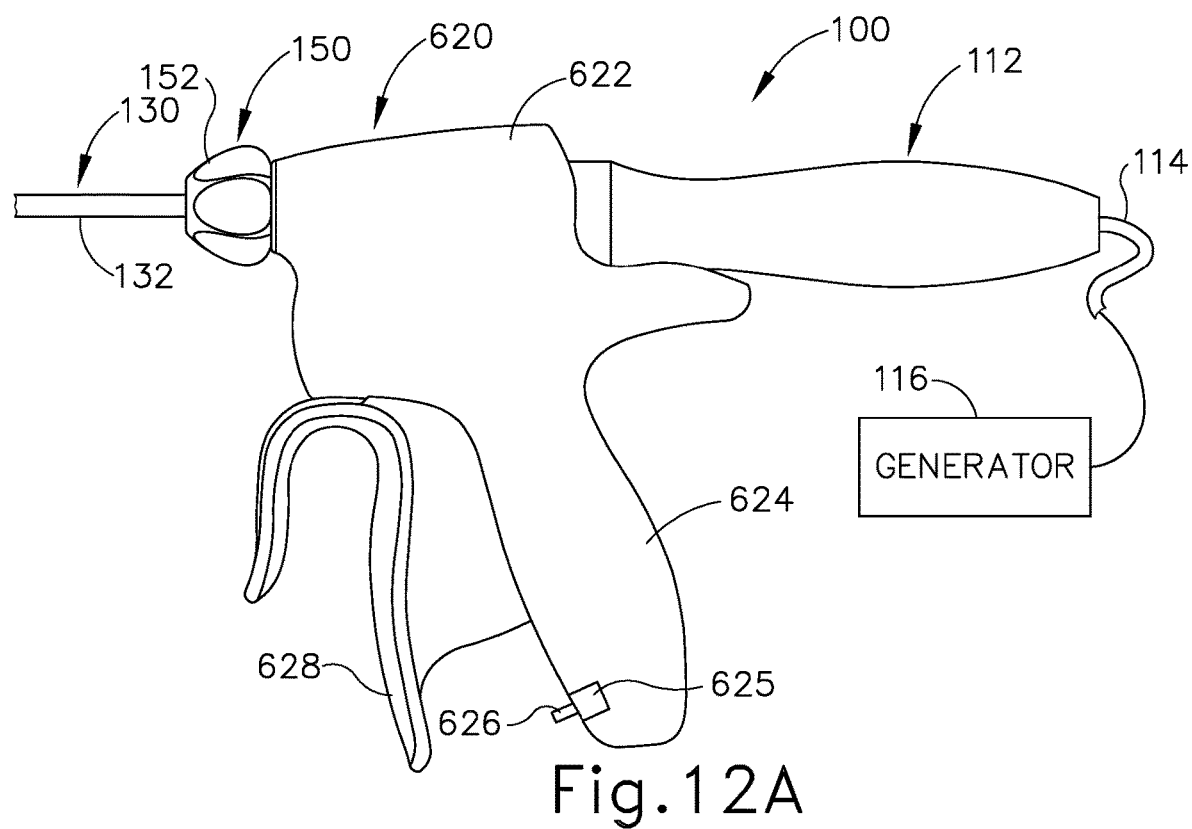
FIG. 12A depicts a side elevational view of another exemplary surgical instrument that may be incorporated into the system of FIG. 1, where the trigger is a in a first position.
Figure 12B:
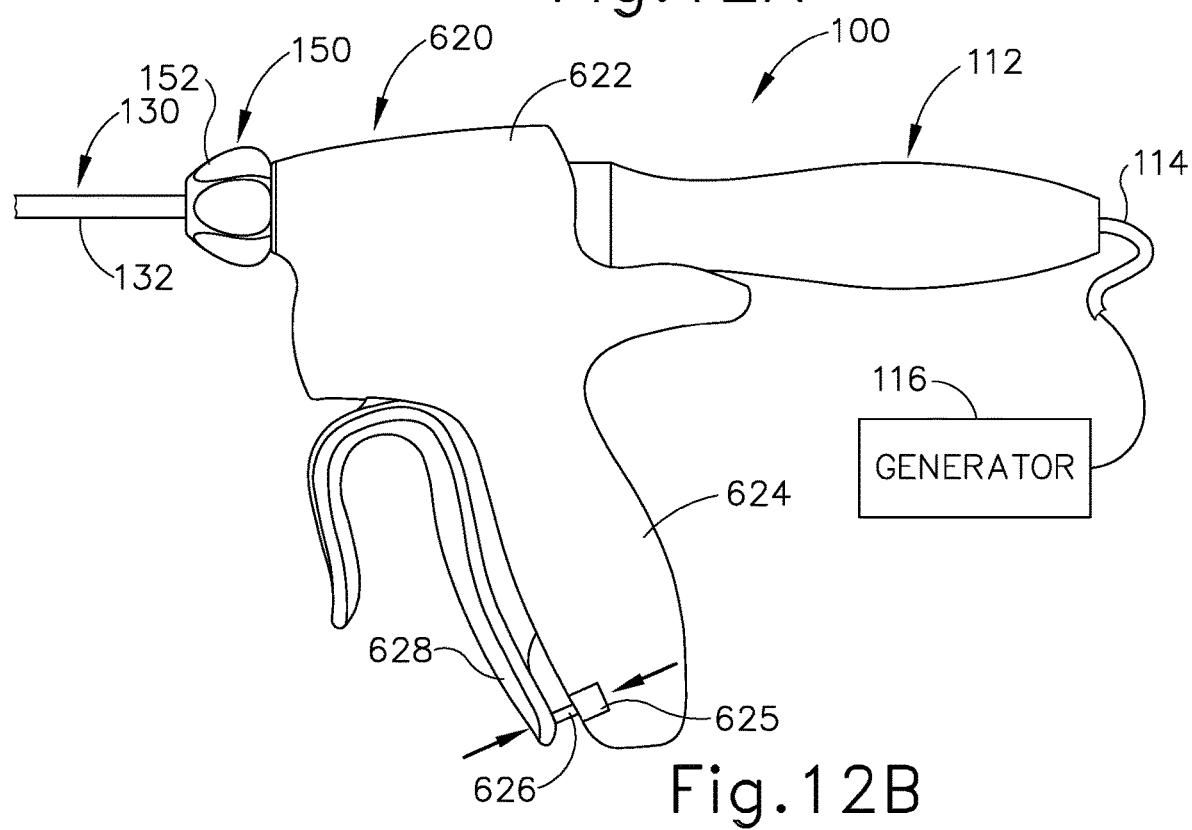
FIG. 12B depicts a side elevational view of the surgical instrument of FIG. 12A, where the trigger is in a second position.
Figure 12C:
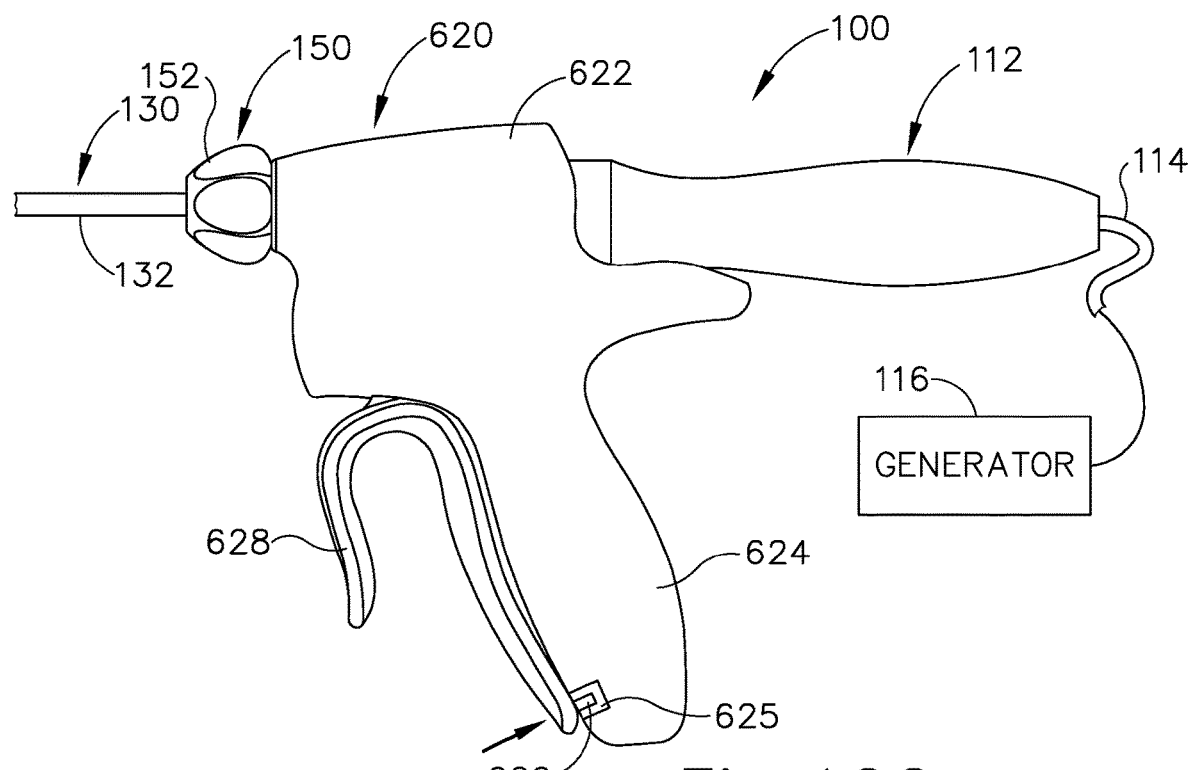
FIG. 12C depicts a side elevational view of the surgical instrument of FIG. 12A, where the trigger is in a third position.

FIGS. 12A-12C show an alternative handle assembly (620) that may be incorporated into ultrasonic surgical instrument (100) described above. Like handle assembly (120), handle assembly (620) of this example includes a body (622), a pistol grip (624), and a trigger (628). These components are substantially similar to body (122), pistol grip (124), and trigger (128) described above, with the differences described below. Handle assembly (620) also receives an ultrasonic transducer (112), just like handle assembly (120) described above. It should be understood that clamp arm (144) may be coupled with trigger (628) such that clamp arm (144) is pivotable toward ultrasonic blade (160) in response to pivoting of trigger (628) toward pistol grip (624); and such that clamp arm (144) is pivotable away from ultrasonic blade (160) in response to pivoting of trigger (628) away from pistol grip (624). Various suitable ways in which clamp arm (144) may be coupled with trigger (628) will be apparent to those of ordinary skill in the art in view of the teachings herein. In some versions, one or more resilient members are used to bias clamp arm (144) and/or trigger (628) to the open position.

While handle assembly (120) includes two activation buttons (126) located on body (122), with one button (126) activating blade (160) at a low power and another button (126) activating blade (160) at a high power; handle assembly (620) of the present example includes only one activation button (626) located on the area of pistol grip (624) facing trigger (628). Activation button (626) is positioned to make contact with the bottom end of trigger (628) when trigger (628) is pivoted almost fully toward pistol grip (624). Activation button (626) is positioned within a damping system (625) that is fixed to pistol grip (624). Damping system (625) of the present example comprises a dashpot that resists motion of activation button (626) via viscous friction. The resistance force imparted by damping system (625) against activation button (626) is proportional to the velocity of button (626). Various suitable components and configurations that may be used to form damping system (625) will be apparent to those of ordinary skill in the art in view of the teachings herein.

Activation button (626) is configured to activate ultrasonic blade (160) once activation button (626) is sufficiently actuated within damping system (625). Therefore, pivoting trigger (628) toward pistol grip (624) will compress activation button (626) within damping system (625) in order to activate ultrasonic blade (160). However, as noted above and as will be described in greater detail below, damping system (625) is configured to at least partially prevent activation of ultrasonic blade (160) if trigger (628) pivots too quickly toward pistol grip (624).

FIG. 12A shows trigger (628) in an open position relative to pistol grip (624), such that trigger (628) does not make contact with activation button (626). FIG. 12B shows trigger (628) pivoting toward pistol grip (624) to initially contact activation button (626). As can be seen, trigger (628) imparts a force to actuate activation button (626) within damping system (625) in an attempt to sufficiently compress activation button (626) within damping system (625) to activate ultrasonic blade (160). However, damping system (625) provides a responding force to the force imparted on activation button (626) by trigger (628). The responding force provided by damping system (625) is proportionate to how quickly trigger (628) rotates toward pistol grip (624). Therefore, if the operator rotates trigger (628) toward pistol grip (624) with too much rotational velocity, damping system (625) will sufficiently prevent activation button (626) from activating ultrasonic blade (160), at least for a moment. However, as shown in FIG. 12C, if the operator rotates trigger (628) toward pistol grip (624) at a rotational velocity where the responding force of damping system (625) cannot sufficiently resist the force imparted on button (626) by trigger (628), then button (626) will sufficiently compress within damping system (62) in order to activate ultrasonic blade (160).

It should be understood that damping system (625) may be implemented in any activation button (126, 226, 326, 426, 626, 726, 926) or any other buttons (572, 1062, 1064, 1066) mentioned herein.

D. Trigger with Two-Stage Closure for Activating Ultrasonic Blade

Figure 13A:
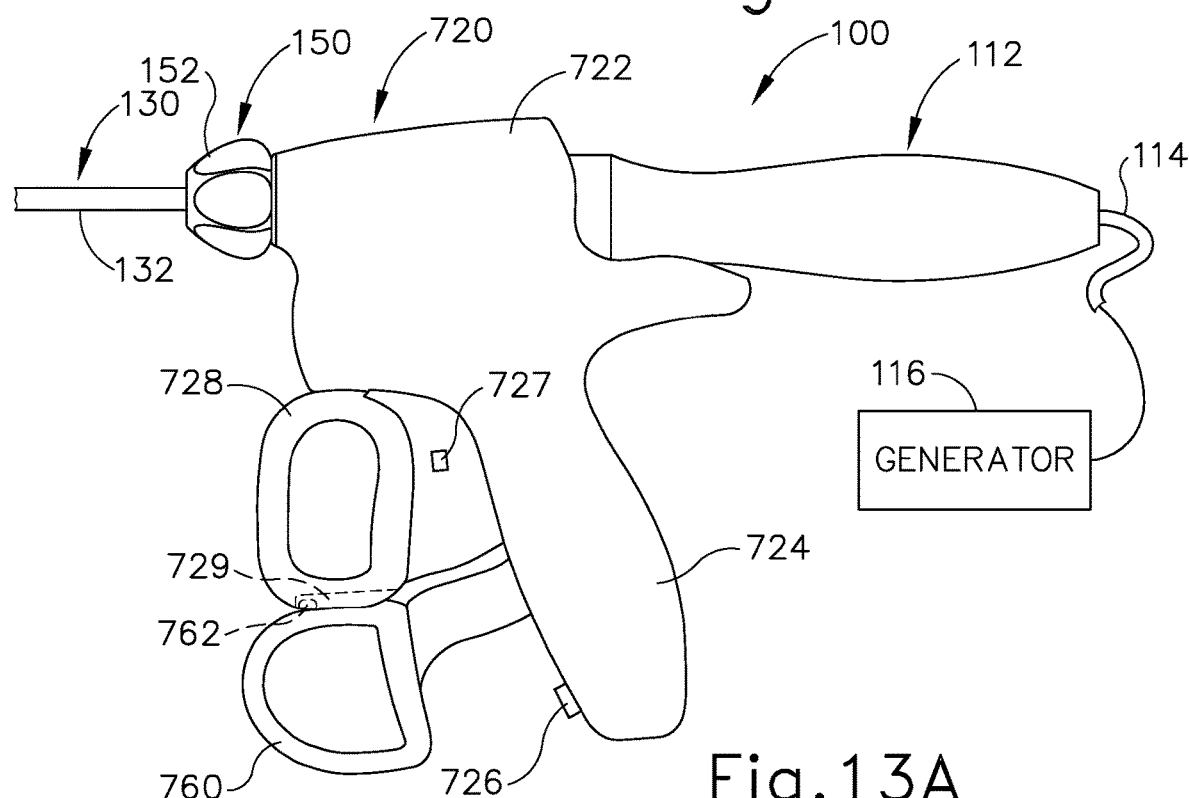
FIG. 13A depicts a side elevational view of another exemplary surgical instrument that may be incorporated into the system of FIG. 1, where the trigger is in a first position.
Figure 13B:
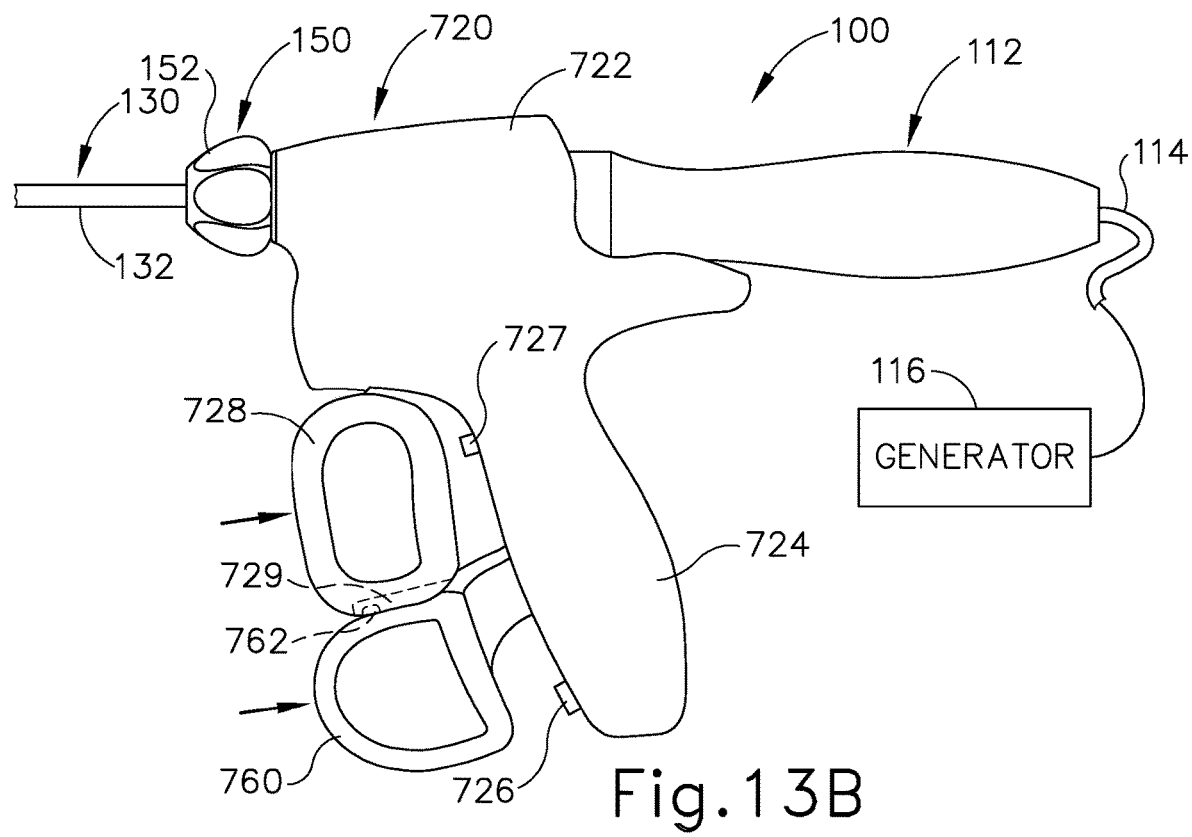
FIG. 13B depicts a side elevational view of the surgical instrument of FIG. 13A, where the trigger is in a second position.
Figure 13C:
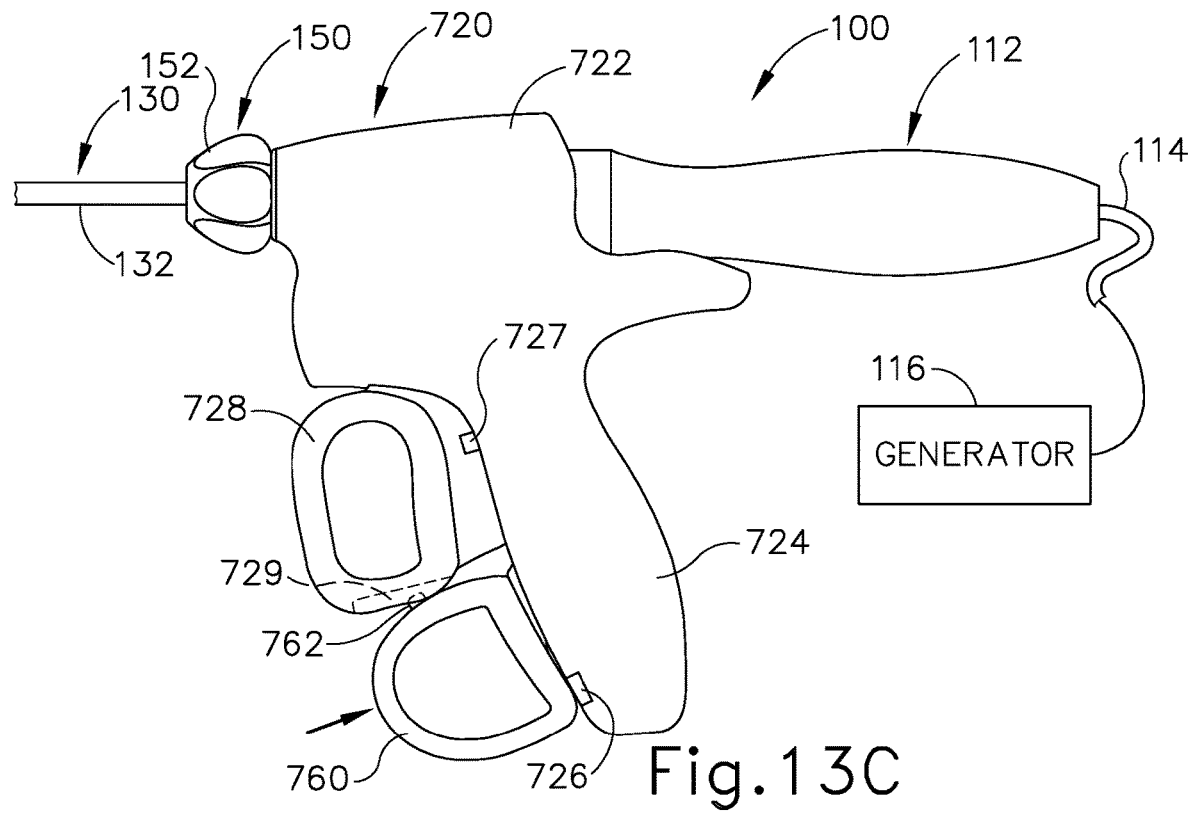
FIG. 13C depicts a side elevational view of the surgical instrument of FIG. 13A, where the trigger is in a third position.

FIGS. 13A-13C show an alternative handle assembly (720) that may be incorporated into ultrasonic surgical instrument (100) described above. Like handle assembly (120), handle assembly (720) of this example includes a body (722), a pistol grip (724), and a trigger (728). These components are substantially similar to body (122), pistol grip (124), and trigger (128) described above, with the differences described below. Handle assembly (720) also receives an ultrasonic transducer (112), just like handle assembly (120) described above. It should be understood that clamp arm (144) may be coupled with trigger (728) such that clamp arm (144) is pivotable toward ultrasonic blade (160) in response to pivoting of trigger (728) toward pistol grip (724); and such that clamp arm (144) is pivotable away from ultrasonic blade (160) in response to pivoting of trigger (728) away from pistol grip (724). Various suitable ways in which clamp arm (144) may be coupled with trigger (728) will be apparent to those of ordinary skill in the art in view of the teachings herein. In some versions, one or more resilient members are used to bias clamp arm (144) and/or trigger (728) to the open position.

While handle assembly (120) includes two activation buttons (126) located on body (122), with one button (126) activating blade (160) at a low power and another button (126) activating blade (160) at a high power, handle assembly (720) of the present example includes only one activation button (726) located on the area of pistol grip (726) facing trigger (728). Handle assembly (720) also includes an activation trigger (760) that is pivotable toward and away from pistol grip (724). As will be described in greater detail below, activation button (726) is positioned within pistol grip (724) to make contact with activation trigger (760) when activation trigger (760) pivots towards pistol grip (724). Activation trigger (760) is thus capable of compressing activation button (726) in order to activate ultrasonic blade (160).

Trigger (728) includes a rotation stop (727) and a slot (729). Activation trigger (760) includes a projection (762) slidably housed within slot (729). By way of example only, slot (729) and projection (762) may have complementary dovetail configurations, complementary "T" shaped configurations, or any other suitable configurations. As seen in FIGS. 13A-13B, trigger and activation trigger (760) are configured to unitarily travel with each other until rotation stop (727) of trigger (728) makes contact with pistol grip (724). Once stop (727) of trigger (728) makes contact with pistol grip (724), trigger (728) is prevented from further rotation toward pistol grip (724). When trigger (728) is rotated to the position shown in FIG. 13B, clamp arm (144) is sufficiently pivoted toward blade (160) to grasp tissue. Once trigger (728) and activation trigger (760) are rotated to the position shown in FIG. 13B, activation button (726) is not yet compressed by activation trigger (760), yet trigger (728) is sufficiently rotated so that end effector (140) may grasp tissue. Therefore, the operator may grasp tissue utilizing handle assembly (720) without yet activating ultrasonic blade (160).

The operator may grasp both trigger (728) and activation trigger (760) to pivot trigger (728) and activation trigger (760) unitarily. Alternatively, the operator may grasp only trigger (728) to pivot both trigger (728) and activation trigger (760) from the position shown in FIG. 13A to the position shown in FIG. 13B. If the operator only grasps trigger (728) to pivot both trigger (728) and activation trigger (760), the distal end of slot (729) may make contact with protrusion (762) to thereby move activation trigger (760) from the position shown in FIG. 13A to the position shown in FIG. 13B.

As shown in FIG. 13C, the operator may further actuate activation trigger (760) relative to trigger (728) after reaching the state shown in FIG. 13B. Protrusion (762) slides within slot (729) or trigger (728), thereby enabling further actuation of activation trigger (760) relative to trigger (728). Activation trigger (760) is configured to actuate toward, and make contact with, pistol grip (724). Activation button (726) is located on a portion of pistol grip (724) facing activation trigger (760), such that complete actuation of activation trigger (760) compresses activation button (726), thereby activation ultrasonic blade (160).

While the present example has trigger (728) and activation trigger (760) slidably coupled together by slot (729) and protrusion (762), any other suitable manner of slidably coupling trigger (728) and activation trigger (760) may be utilized. For example, trigger (728) and activation trigger (760) may be coupled by a spring that biases trigger (728) and activation trigger (760) together. In such versions, activation trigger (760) may travel from the position shown in FIG. 13B to the position shown in FIG. 13C by the operator overcoming the biasing force coupling trigger (728) and activation trigger (760).

Figure 14A:
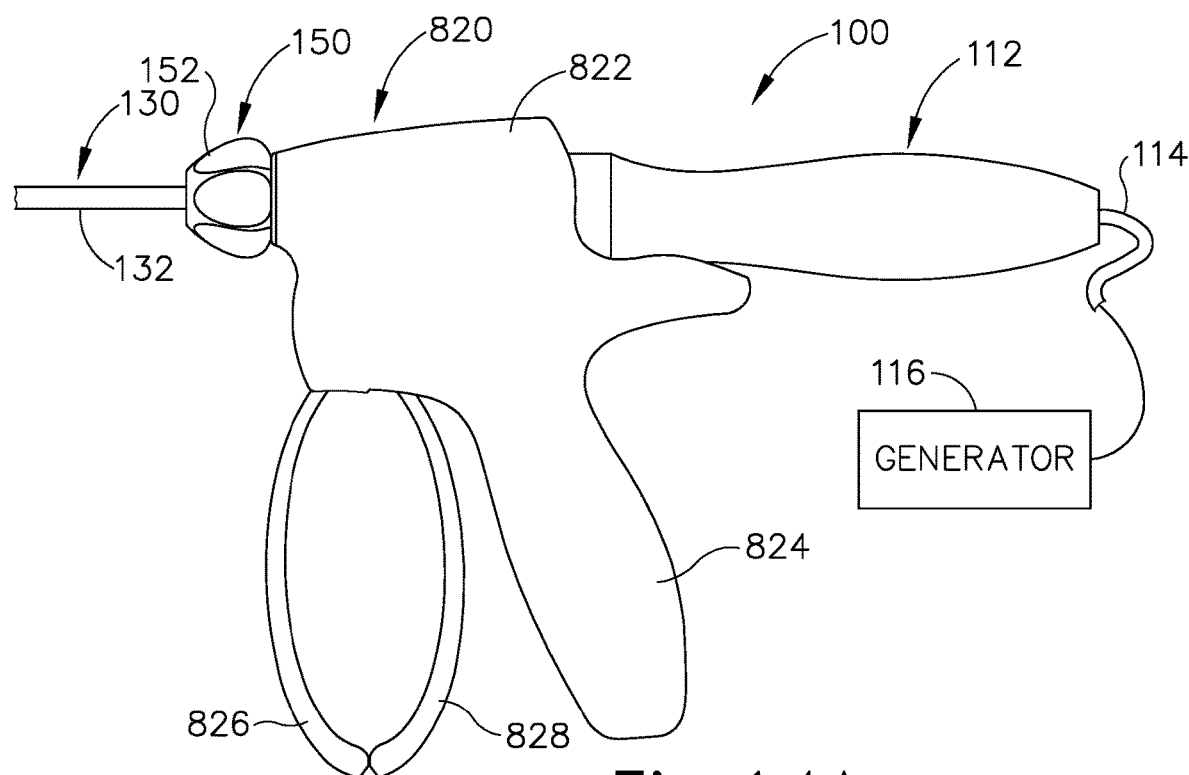
FIG. 14A depicts a side elevational view of another exemplary surgical instrument that may be incorporated into the system of FIG. 1, where the trigger is in a first position.
Figure 14B:
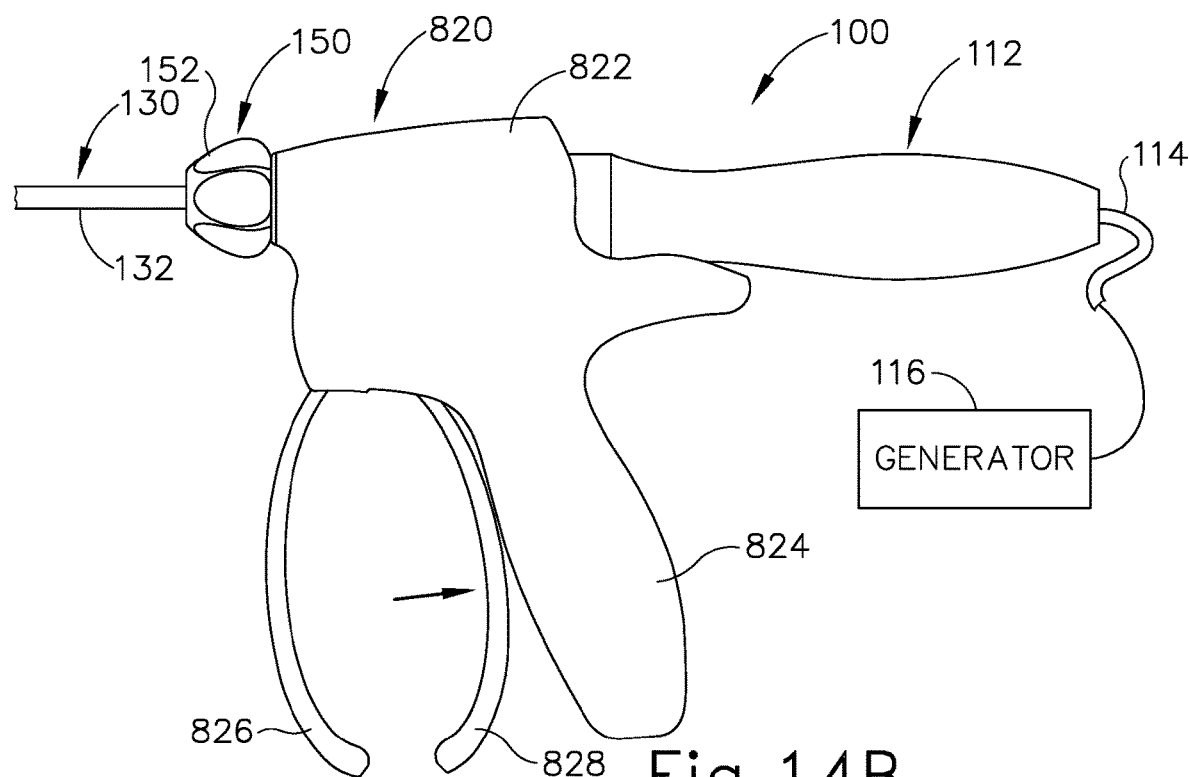
FIG. 14B depicts a side elevational view of the surgical instrument of FIG. 14A, where the trigger is in a second position.
Figure 14C:
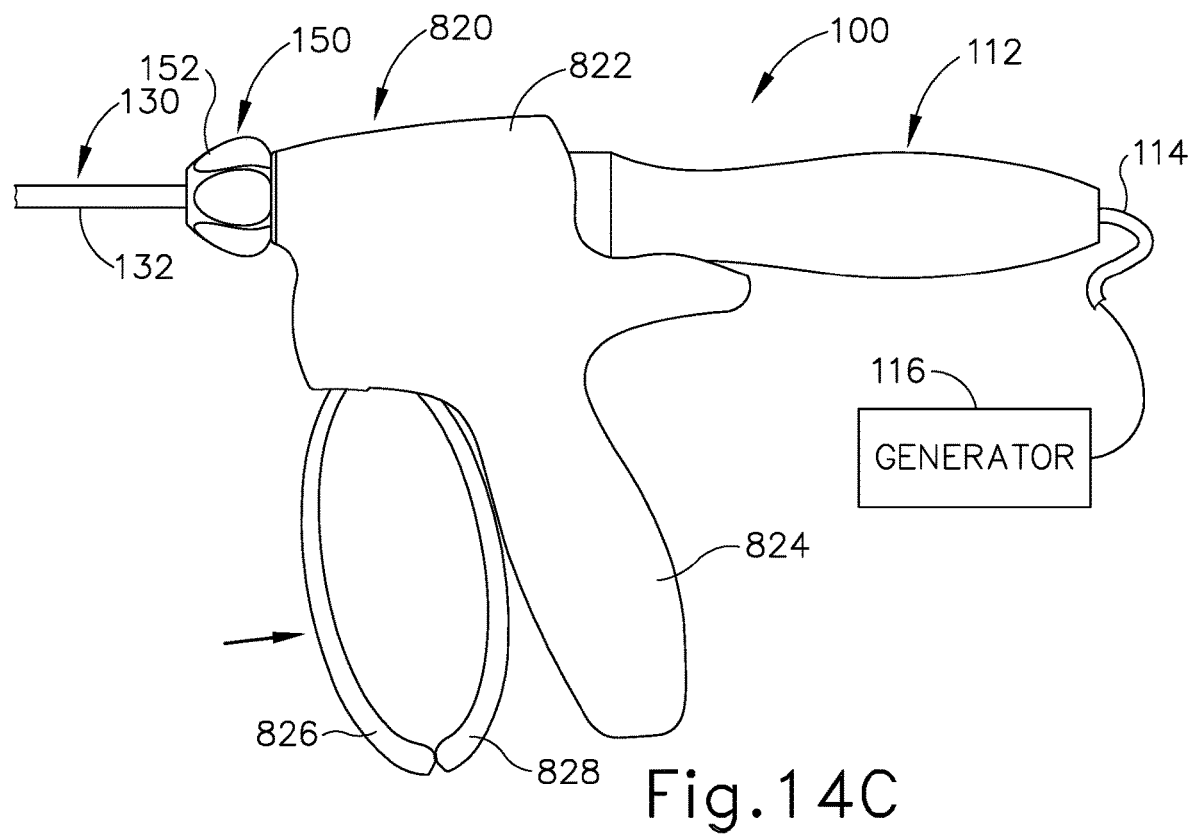
FIG. 14C depicts a side elevational view of the surgical instrument of FIG. 14A, where the trigger is in a third position.

FIGS. 14A-14C show an alternative handle assembly (820) that may be incorporated into ultrasonic surgical instrument (100) described above. Like handle assembly (120), handle assembly (820) of this example includes a body (822), a pistol grip (824), and a trigger (828). These components are substantially similar to body (122), pistol grip (124), and trigger (128) described above, with the differences described below. Handle assembly (820) also receives an ultrasonic transducer (112), just like handle assembly (120) described above. It should be understood that clamp arm (144) may be coupled with trigger (828) such that clamp arm (144) is pivotable toward ultrasonic blade (160) in response to pivoting of trigger (828) toward pistol grip (824); and such that clamp arm (144) is pivotable away from ultrasonic blade (160) in response to pivoting of trigger (828) away from pistol grip (824). Various suitable ways in which clamp arm (144) may be coupled with trigger (828) will be apparent to those of ordinary skill in the art in view of the teachings herein. In some versions, one or more resilient members are used to bias clamp arm (144) and/or trigger (828) to the open position.

While handle assembly (120) includes two activation buttons (126) located on body (122), with one button (126) activating blade (160) at a low power and another button (126) activating blade (160) at a high power; handle assembly (820) of the present example has no activation button. Instead, handle assembly (820) of this example has an activation trigger (826). Trigger (828) is pivotable toward and away from pistol grip (824) independently of activation trigger (826). Activation trigger (826) is located distally in relation to trigger (828). The bottom ends of trigger (828) and activation trigger (826) are in contact in the position shown in FIG. 14A in this example. However, this relationship is merely optional, as ends of trigger (828) and activation trigger (826) may be distanced apart from one another in some other variations.

FIG. 14A shows trigger (828) in the open position. With trigger (282) at the position shown in FIG. 14A, clamp arm (144) is pivoted away from ultrasonic blade (160). Additionally, activation trigger (826) is also in the open position. When activation trigger (826) is in the open position, ultrasonic blade (160) is not activated.

As shown in FIGS. 14A-14B, trigger (828) may pivot toward pistol grip (824) in order to pivot clamp arm (144) toward ultrasonic blade (160). At the position shown in FIG. 14B, end effector (140) is capable of grasping tissue. Additionally, activation trigger (826) is still in the open position. Therefore, ultrasonic blade (160) is not yet activated. The operator may thus pivot trigger (828) toward pistol grip (824) in order to grasp and manipulate tissue without activating ultrasonic blade (160). Trigger (828) may also be selectively latched closed so that the operator no longer has to grasp trigger (828) in order to grasp tissue with end effector (140).

As shown in FIG. 14C, activation trigger (826) is rotated toward pistol grip (824) while trigger (828) remains pivoted toward pistol grip (824). At this position, activation trigger (826) is rotated to an "activated" position, thereby activating ultrasonic blade (160). While current FIGS. 14A-14C show trigger (828) pivoting toward pistol grip (824) first to grasp tissue, and then activation trigger (826) pivoting toward pistol grip (824) independently to activate ultrasonic blade (160), the operator may choose to simply actuate activation trigger (826) to thereby rotate both trigger (828) and activation trigger (826) simultaneously, to thereby grasp tissue and activate ultrasonic blade (160) simultaneously.

It should be understood that activation trigger (826) may be utilized in place of activation button (126, 226, 326, 426, 526, 626, 726, 926) in handle assembly (120, 220, 320, 420, 520, 620, 720, 920) respectively.

E. Trigger with Lateral Adjustment for Mode Defining Positions

FIGS. 15A-18B show an alternative handle assembly (920) that may be incorporated into ultrasonic surgical instrument (100) described above. Like handle assembly (120), handle assembly (920) of this example includes a body (922), a pistol grip (924), and a trigger (928). These components are substantially similar to body (122), pistol grip (124), and trigger (128) described above, with the differences described below. Handle assembly (920) also receives an ultrasonic transducer (112), just like handle assembly (120) described above. It should be understood that clamp arm (144) may be coupled with trigger (928) such that clamp arm (144) is pivotable toward ultrasonic blade (160) in response to pivoting of trigger (928) toward pistol grip (924); and such that clamp arm (144) is pivotable away from ultrasonic blade (160) in response to pivoting of trigger (928) away from pistol grip (924). Various suitable ways in which clamp arm (144) may be coupled with trigger (928) will be apparent to those of ordinary skill in the art in view of the teachings herein. In some versions, one or more resilient members are used to bias clamp arm (144) and/or trigger (928) to the open position.

As will be described in greater detail below, trigger (928) is configured to pivot along two different dimensions. In particular, trigger (928) is configured to pivot along a first dimension toward and away from pistol grip (924), just like the other triggers described herein. However, unlike the other triggers described herein, trigger (928) of the present example is also configured to pivot along a second dimension that is perpendicular to the first dimension. In other words, trigger (928) is operable to pivot along a plane that is laterally oriented relative to the longitudinal axis of shaft assembly (130); in addition to being operable to pivot along a plane that is parallel to the longitudinal axis of shaft assembly (130).

While handle assembly (120) includes two activation buttons (126) located on body (122), with one button (126) activating blade (160) at a low power and another button (126) activating blade (160) at a high power; handle assembly (920) includes only one activation button (926). In addition, body (922) of the present example houses a mode selection frame (960) having three individual power switches (961, 963, 965). Trigger (928) is fixed to a projection (970) that extends through a slot (923) of body (922). A bridge (972) is attached to the top of projection (970). Bridge (972) is housed within mode selection frame (960). As will be described in greater detail below, bridge (972) is configured to make contact with an individual power switch (961, 963, 965) to determine the power level at which ultrasonic blade (160) operates.

Figure 15A:
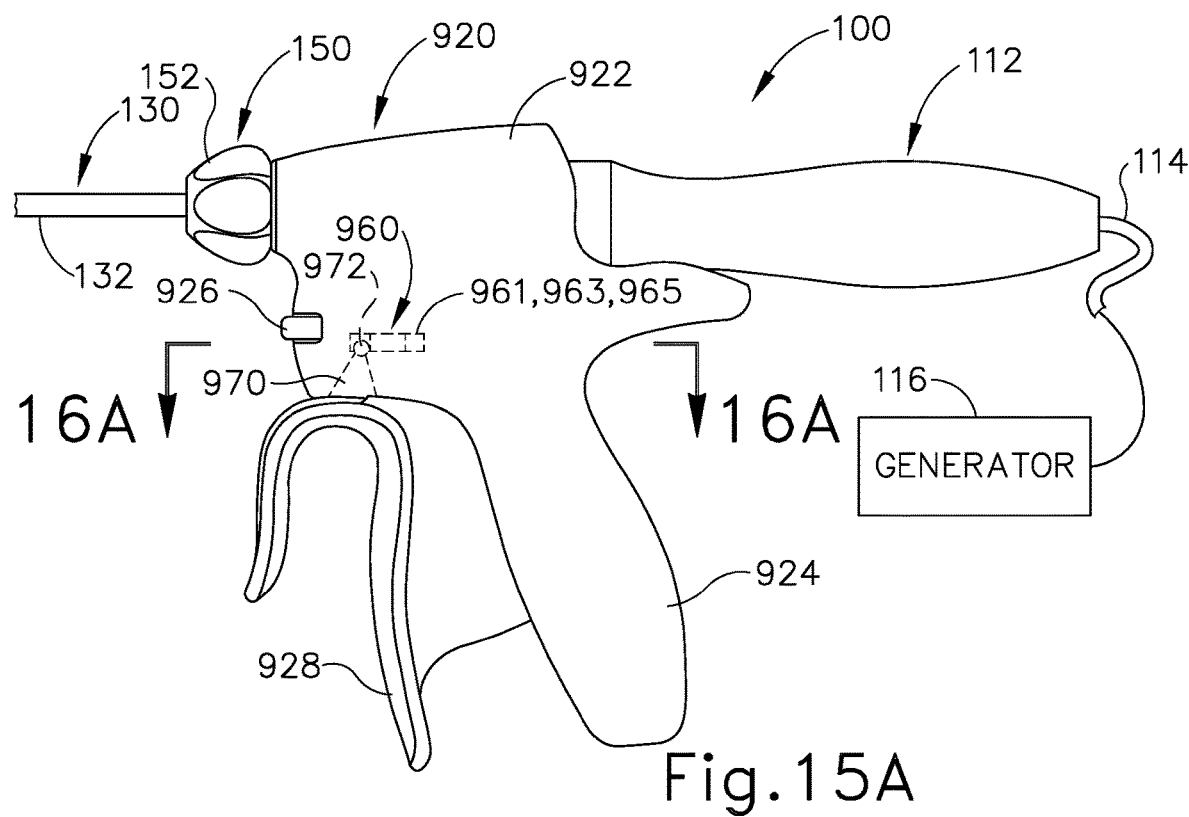
FIG. 15A depicts a side elevational view of another surgical instrument that may be incorporated into the system of FIG. 1, where the trigger is in a first longitudinal position.
Figure 15B:
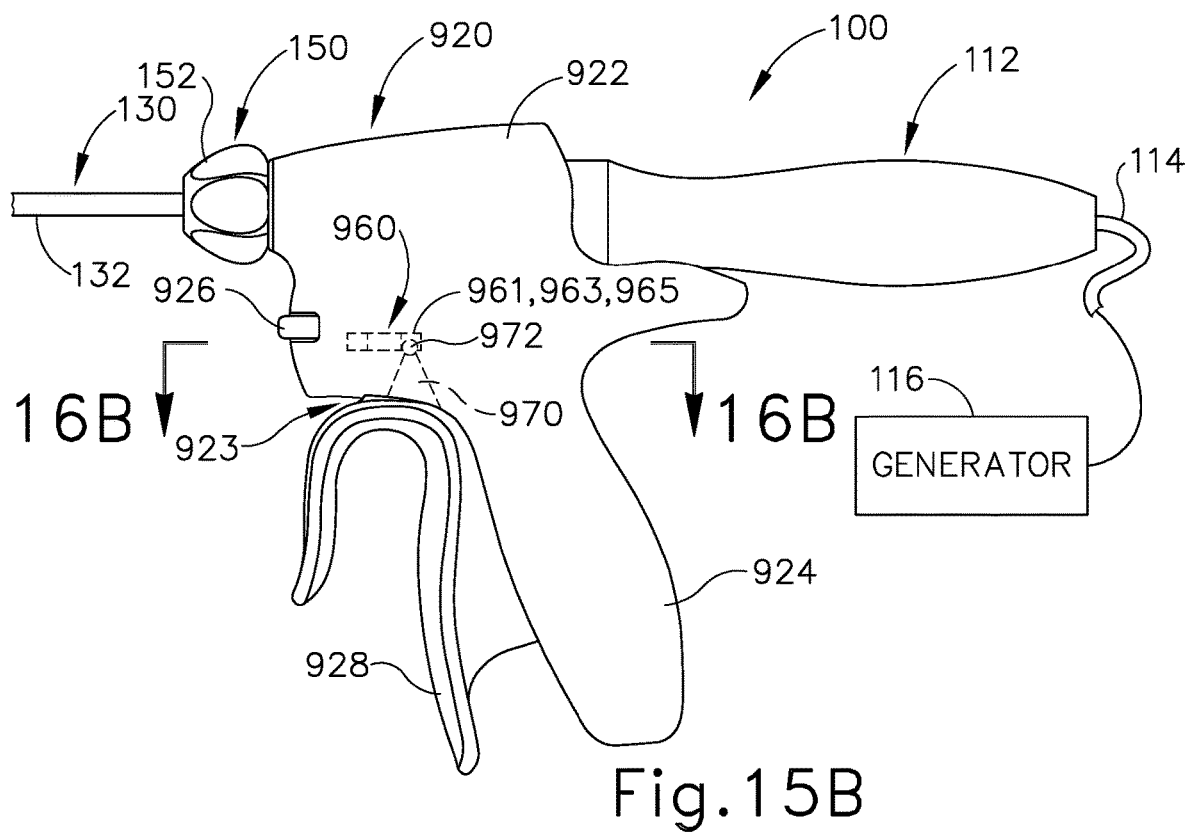
FIG. 15B depicts a side elevational view of the surgical instrument of FIG. 15A, where the trigger is in a second longitudinal position.

As can be seen in FIGS. 15A-15B, bridge (972) is located within mode selection frame (960) such that as trigger (928) pivots toward pistol grip (924), bridge (972) travels within mode selection frame (960) to make contact with one of power switches (961, 963, 965). As will be described in greater detail below, bridge (972) may only activate one power switch (961, 963, 965) at a time, corresponding to the lateral pivoting location of trigger (928) relative to body (922). Individual switches (961, 963, 965) are in electrical communication with circuit board (34). Activation of individual switches (961, 963, 965) via contact with bridge (972) will effect a selection of a power mode in circuit board (34). Thus, when button (926) is activated while bridge (972) makes contact with an individual switch (961, 963, 965), transducer (112) will provide a corresponding power level or amplitude of ultrasonic energy to ultrasonic blade (160) based on a control signal from circuit board (34).

Trigger (928) may pivot laterally relative to body (922) within slot (923). As mentioned above, projection (970) extends within body (922) through slot (923). Therefore, projection (970) is located above slot (923), while trigger (928) is located below slot (923). When trigger (928) pivots laterally to the left of body (922) below slot (923), projection (970) pivots laterally to the right of body (922) above slot (923). As mentioned above, bridge (972) is fixed to the top of projection (970), such that bridge (972) pivots laterally relative to body (922) with projection (970).

As can be seen in FIGS. 16A-18B, mode selection frame (960) defines a lateral deflection channel (968), a low guide channel (962) a medium guide channel (964), and a high guide channel (966). As will be discussed in greater detail below, bridge (972) is housed within mode selection frame (960) such that bridge (972) may travel within each channel (962, 964, 966, 968). Low switch (963) is fixed at the proximal end of low guide channel (962). Medium switch (965) is fixed at the proximal end of medium guide channel (964). High switch (967) is fixed at the proximal end of high guide channel (966).

Figure 16A:
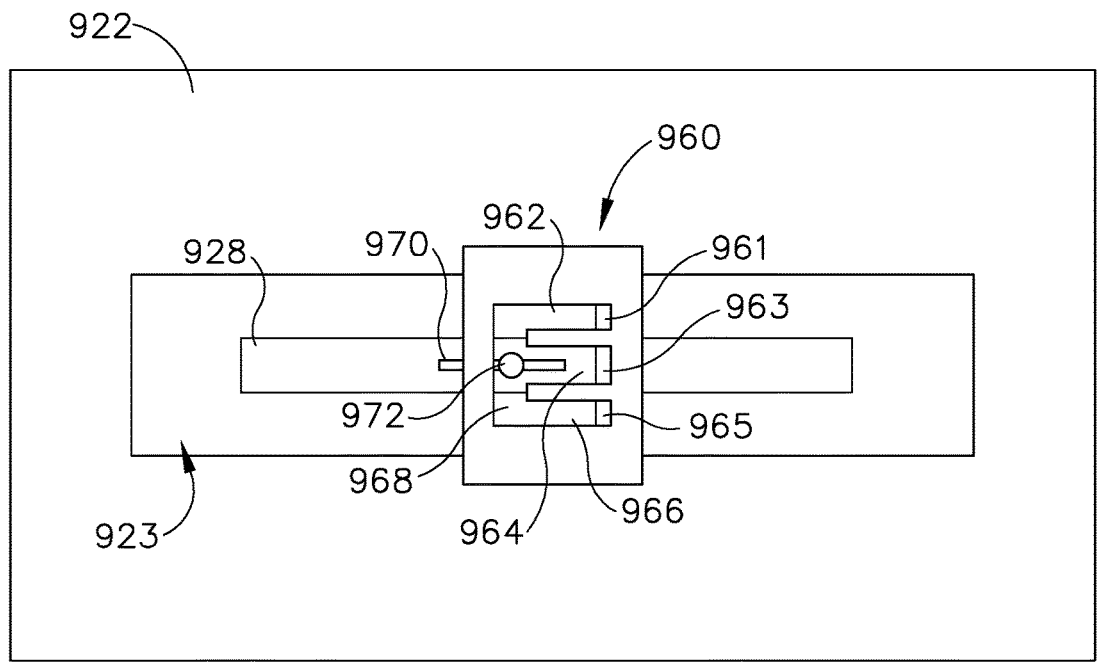
FIG. 16A depicts a cross-sectional view of the surgical instrument of FIG. 15A taken along line 16A-16A of FIG. 15A, where the trigger is in a first lateral position.
Figure 16B:
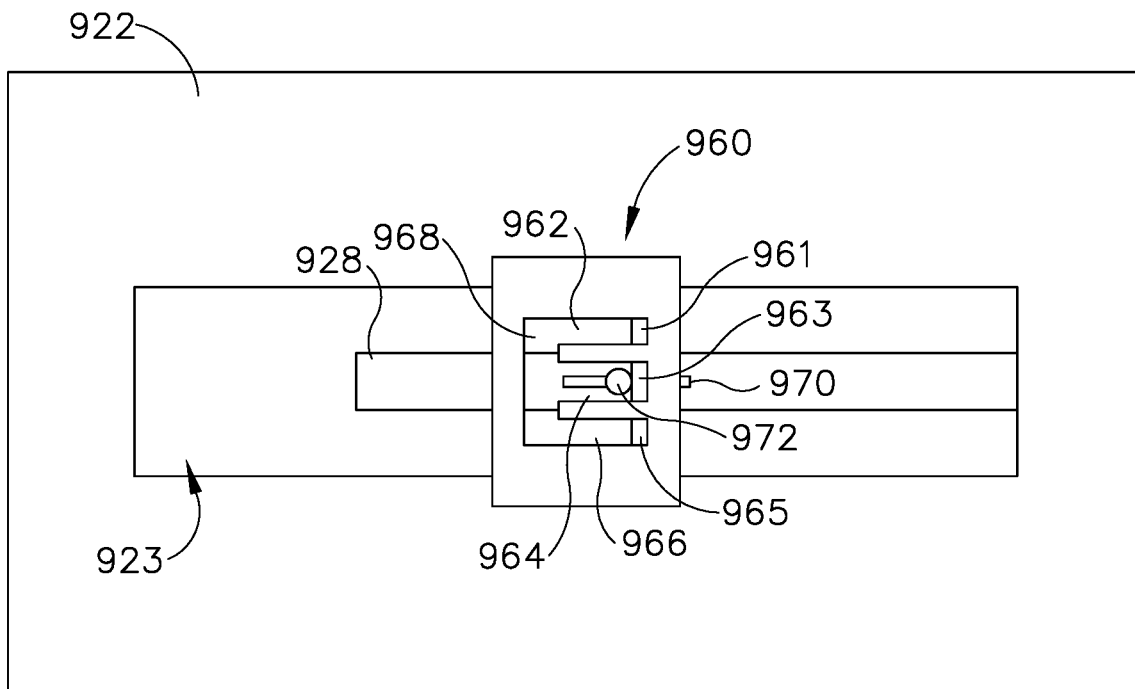
FIG. 16B depicts a cross-sectional view of the surgical instrument of FIG. 15A taken along the line 16B-16B of FIG. 15B, where the trigger in a first lateral position.

As shown in FIGS. 15A, 16A, 17A, and 18A, when trigger (928) is in the open position relative to pistol grip (924), bridge (972) is located within lateral deflection channel (968) of mode selection frame (960). Trigger (928) is operable to pivot laterally when bridge (972) is located within lateral deflection channel (968). FIG. 16A shows trigger (928), projection (970), and bridge (972) having no lateral deflection relative to body (922). Bridge (972) is therefore longitudinally aligned with medium guide channel (964). FIG. 16B shows trigger (928) pivoted toward pistol grip (924), as also shown in FIG. 15B. Because trigger (928) is not laterally deflected to rotate about slot (923), bridge (972) longitudinally travels in the proximal direction within medium guide channel (964) to make contact with medium switch (965). At this point, medium switch (963) is activated by making contact with bridge (972). Medium switch (963) thereby communicates a medium power level to circuit board (34). Thus, activation of button (926) while bridge (972) is in contact with medium switch (963) will activate ultrasonic blade (160) at a medium power level.

Figure 17A:
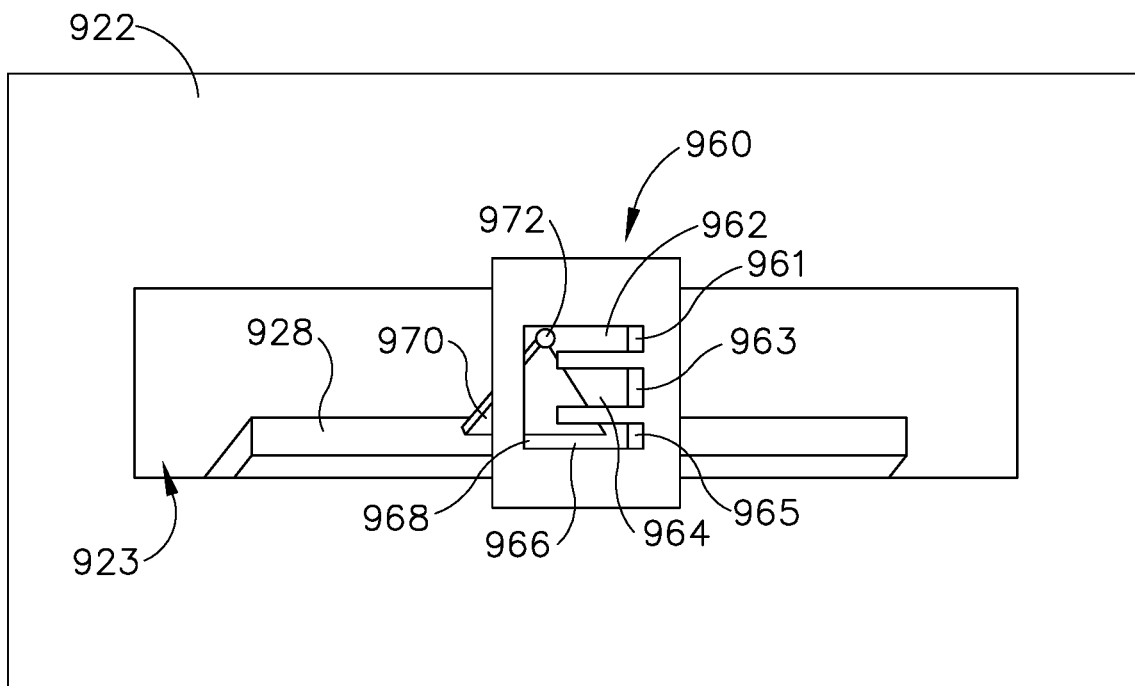
FIG. 17A depicts a cross-sectional view of the surgical instrument of FIG. 15A taken along line 16A-16A of FIG. 15A, where the trigger is in a second lateral position.
Figure 17B:
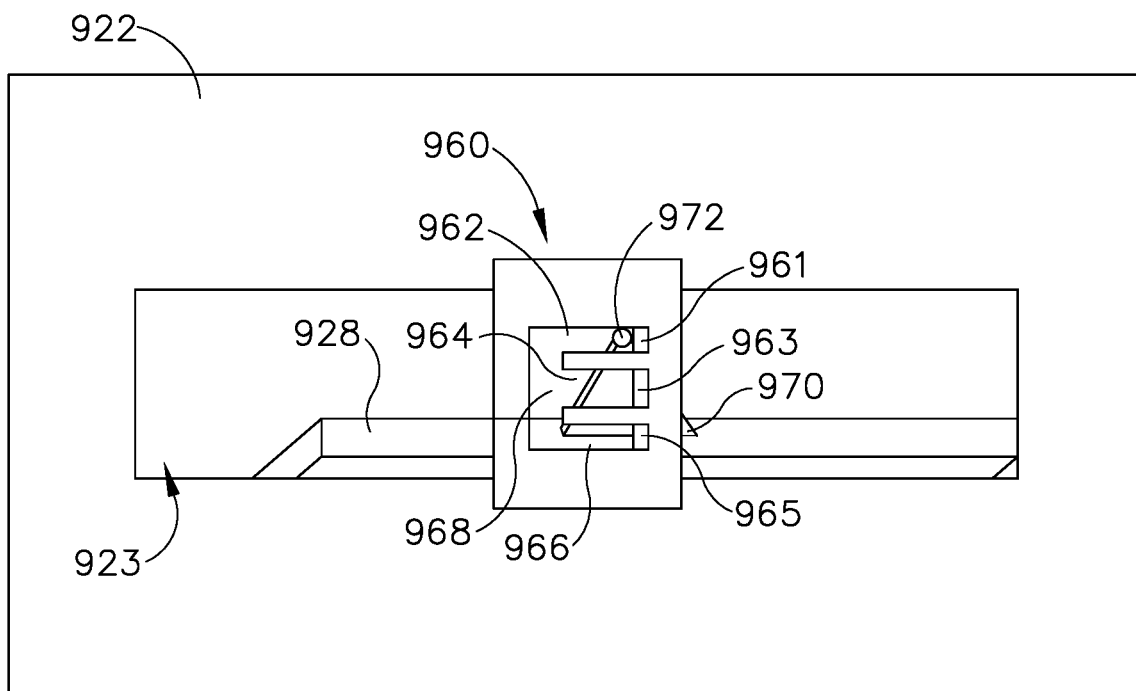
FIG. 17B depicts a cross-sectional view of the surgical instrument of FIG. 15A taken along line 16B-16B of FIG. 15B, where the trigger is in a second lateral position.

FIG. 17A shows trigger (928) pivoted laterally to the left of body (922) below slot (923). Therefore, projection (970) and bridge (972) are laterally rotated to the right relative to body (922) above slot (923). Bridge (972) is therefore longitudinally aligned with low guide channel (962) in this state. FIG. 17B shows trigger (928) pivoted toward pistol grip (924), as also shown in FIG. 15B. Bridge (972) longitudinally travels in the proximal direction within low guide channel (962) to make contact with low switch (961). At this point, low switch (961) is activated by making contact with bridge (972). Low switch (961) thereby communicates a low power level to circuit board (34). Thus, activation of button (926) while bridge (972) is in contact with low switch (961) will activate ultrasonic blade (160) at a low power level.

Figure 18A:
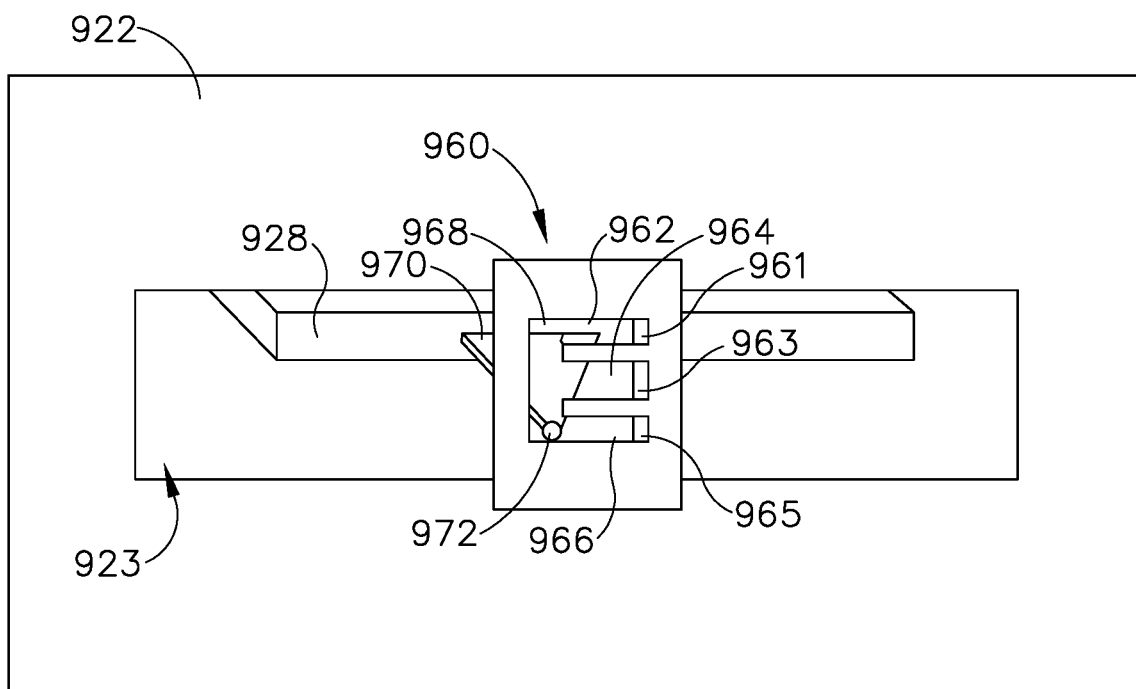
FIG. 18A depicts a cross-sectional view of the surgical instrument of FIG. 15A taken along line 16A-16A of FIG. 15A, where the trigger is in a third lateral position.
Figure 18B:
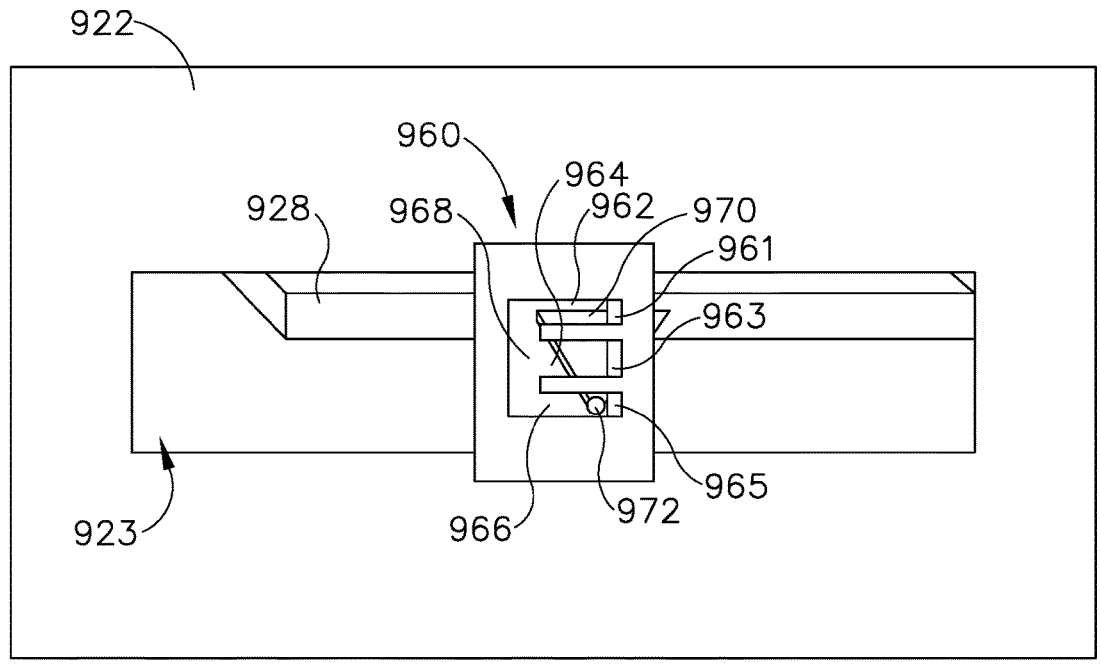
FIG. 18B depicts a cross-sectional view of the surgical instrument of FIG. 15A taken along line 16B-16B of FIG. 15B, where the trigger is in a third lateral position.

FIG. 18A shows trigger (928) pivoted laterally to the right of body (922) below slot (923). Therefore, projection (970) and bridge (972) are laterally rotated to the left relative to body (922) above slot (923). Bridge (972) is therefore longitudinally aligned with high guide channel (966) in this state. FIG. 18B shows trigger (928) pivoted toward pistol grip (924), as also shown in FIG. 15B. Bridge (972) longitudinally travels in the proximal direction within high guide channel (966) to make contact with high switch (965). At this point, high switch (965) is activated by making contact with bridge (972). High switch (965) thereby communicates a high power level to circuit board (34). Thus, activation of button (926) while bridge (972) is in contact with high switch (965) will activate ultrasonic blade (160) at a high power level.

While the current example shows trigger (928) pivoting laterally within slot (923) relative to body (922), it is envisioned that trigger (928) may alternatively translate laterally within slot (923) relative to body (922). Therefore, if trigger (928) is translated laterally to the right below slot (923), projection (970) and bridge (972) will also translate laterally to the right above slot (923).

F. Tri-Lever Trigger

Figure 19A:
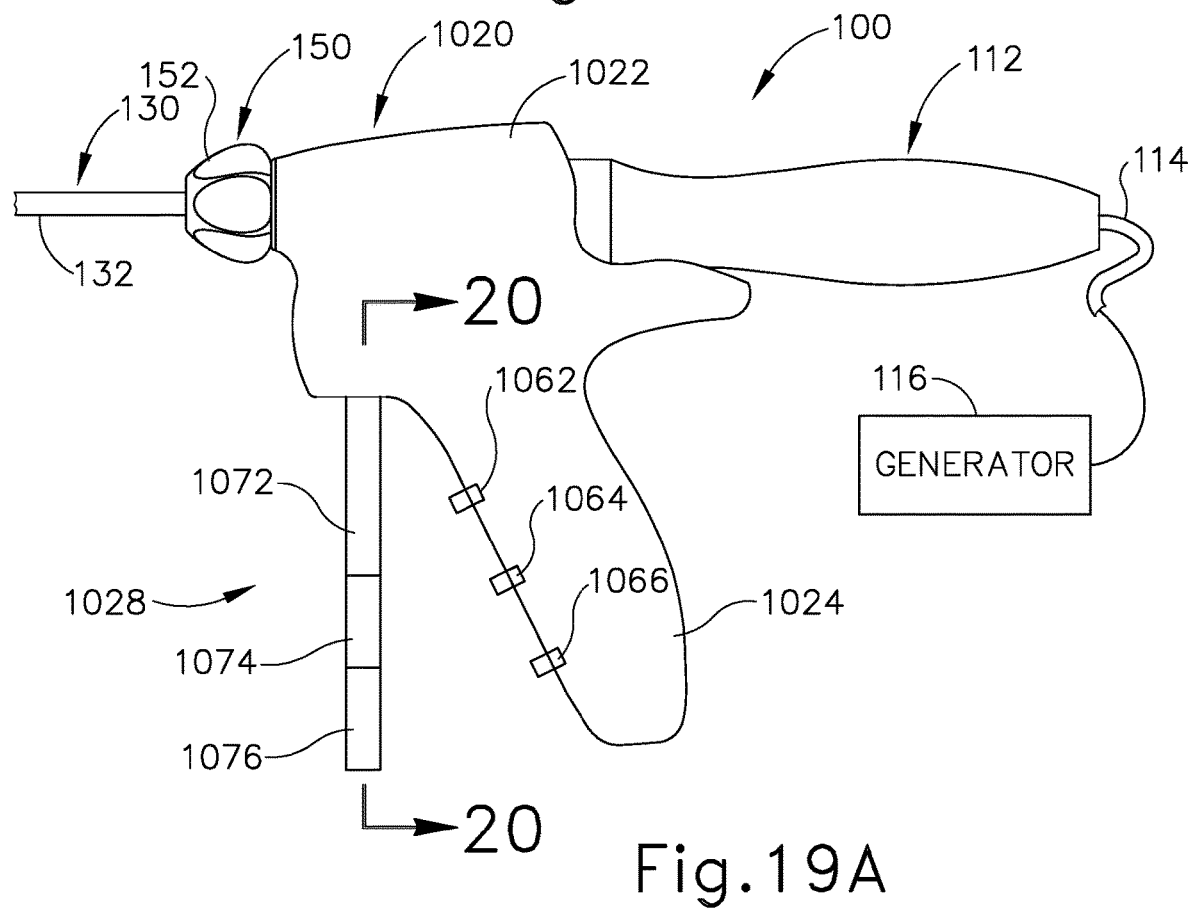
FIG. 19A depicts a side elevational view of another exemplary surgical instrument that may be incorporated into the system of FIG. 1, where the trigger is in a first position.
Figure 19B:
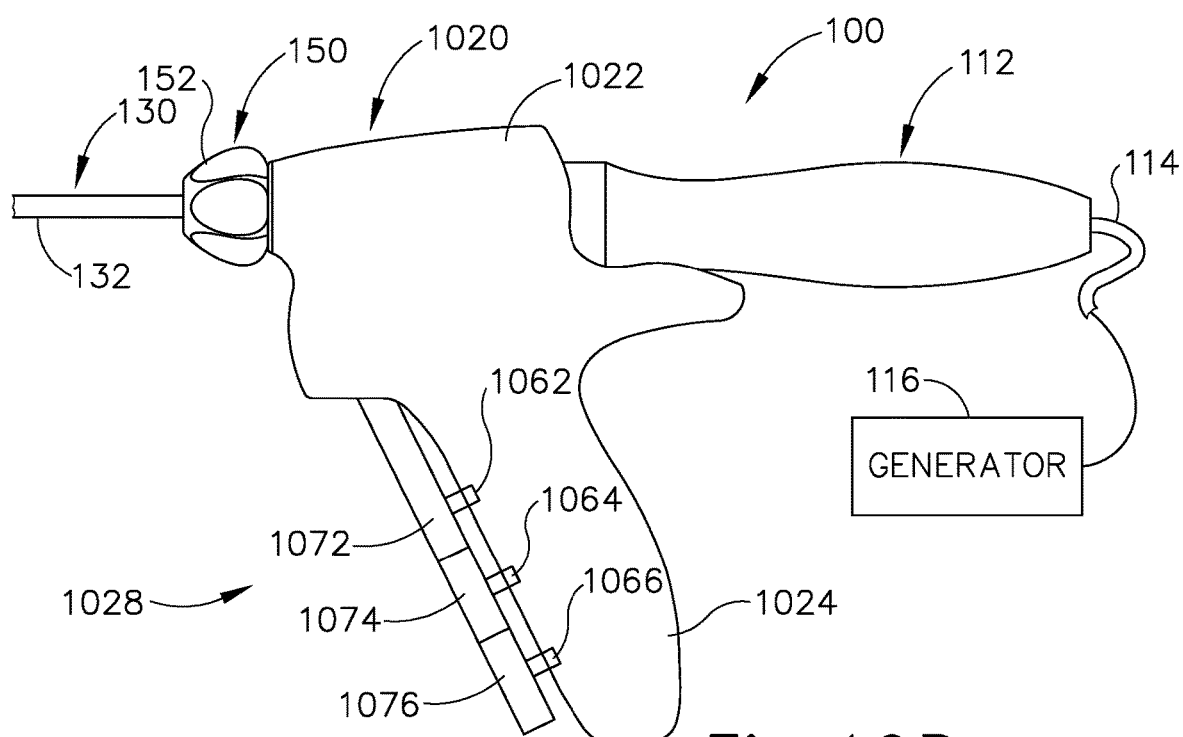
FIG. 19B depicts a side elevational view of the surgical instrument of FIG. 19A, were the trigger is in a second position.
Figure 19C:
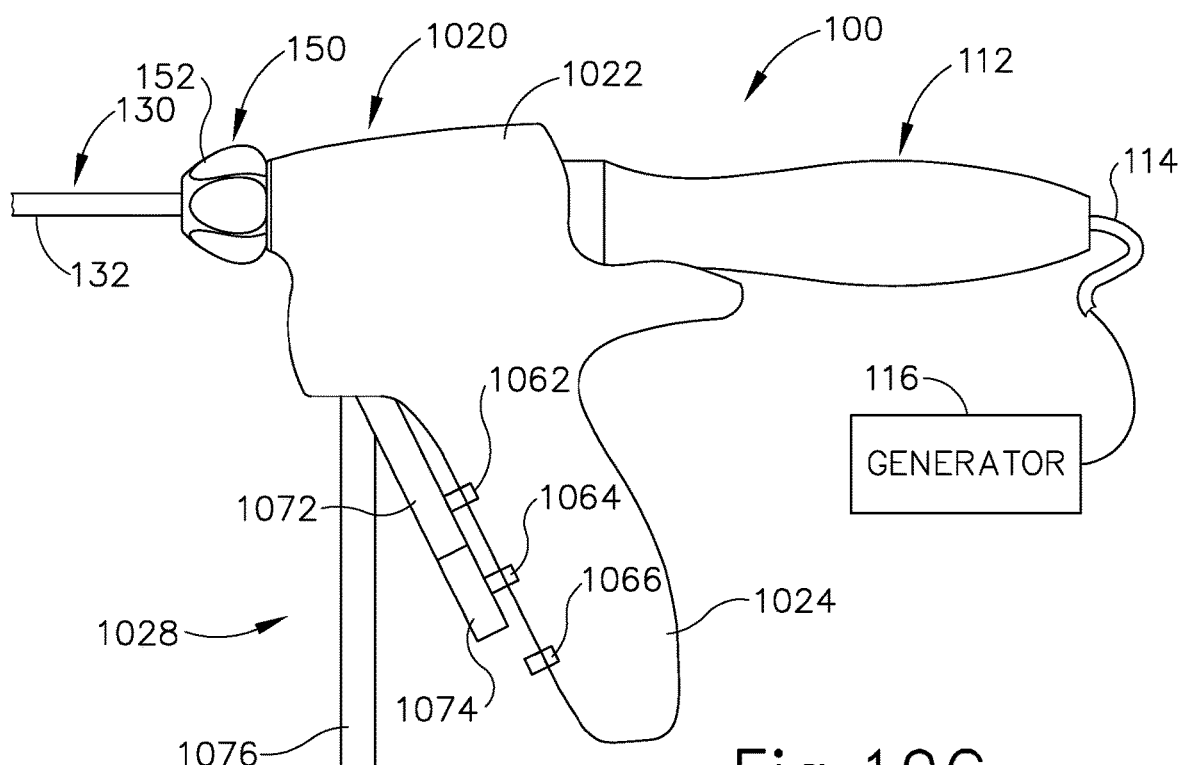
FIG. 19C depicts a side elevational view of the surgical instrument of FIG. 19A, where the trigger is in a third position.
Figure 19D:
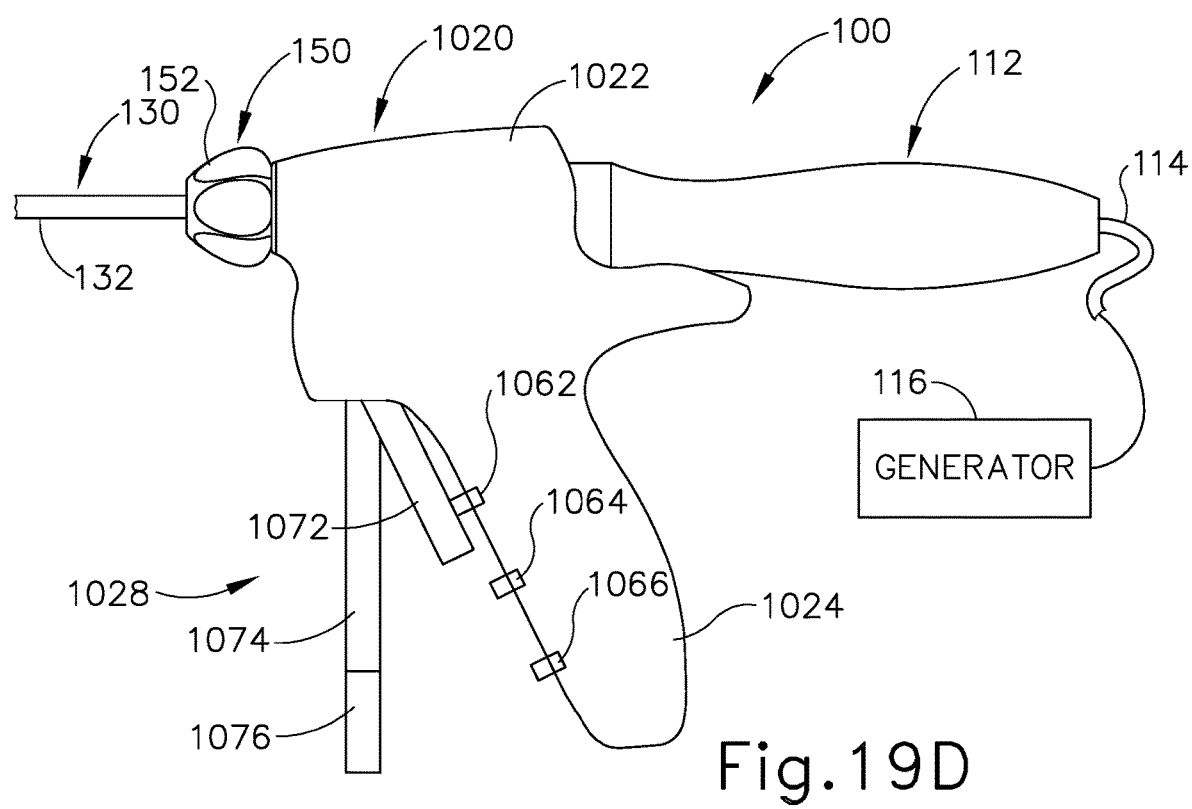
FIG. 19D depicts a side elevational view of the surgical instrument of FIG. 19A, where the trigger is in a fourth position.
Figure 20:
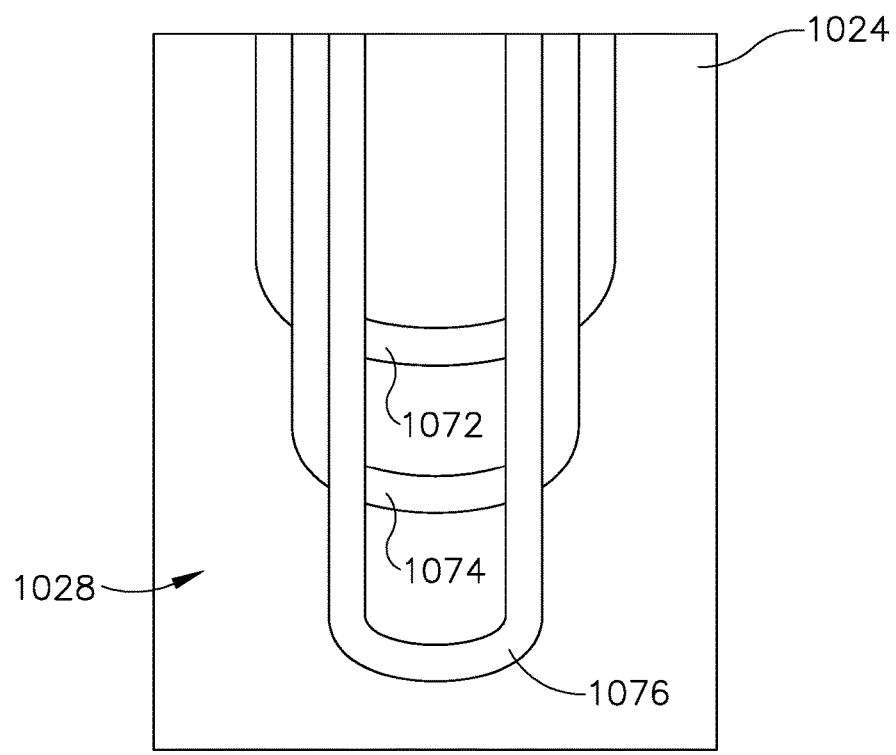
FIG. 20 depicts a cross-sectional view of the surgical instrument of FIG. 19A taken along line 20-20 of FIG. 19A.

FIGS. 19A-20 show an alternative handle assembly (1020) that may be incorporated into ultrasonic surgical instrument (100) described above. Like handle assembly (120), handle assembly (1020) of this example includes a body (1022), a pistol grip (1024), and a trigger (1028). These components are substantially similar to body (122), pistol grip (124), and trigger (128) described above, with the differences described below. Handle assembly (1020) also receives an ultrasonic transducer (112), just like handle assembly (120) described above. It should be understood that clamp arm (144) may be coupled with trigger (1028) such that clamp arm (144) is pivotable toward ultrasonic blade (160) in response to pivoting of trigger (1028) toward pistol grip (1024); and such that clamp arm (144) is pivotable away from ultrasonic blade (160) in response to pivoting of trigger (1028) away from pistol grip (1024). Various suitable ways in which clamp arm (144) may be coupled with trigger (1028) will be apparent to those of ordinary skill in the art in view of the teachings herein. In some versions, one or more resilient members are used to bias clamp arm (144) and/or trigger (1028) to the open position.

Trigger assembly (1028) of the present example comprise a tri-lever trigger that is pivotally coupled to body (1022) such that trigger assembly (1028) is capable of pivoting toward and away from pistol grip (1024). In some versions, one or more resilient members are used to bias trigger assembly (1028) to the open position, as shown in FIGS. 19A and 20. Trigger assembly (1028) includes a short trigger (1072), a medium trigger (1074), and a long trigger (1076). As best seen in FIG. 20, individual triggers (1072, 1074, 1076) are in a stacked arrangement. In particular, short trigger (1072) is located proximally in relation to medium trigger (1074), which is located proximally in relation to long trigger (1076). Thus, pivoting long trigger (1076) toward pistol grip (1024) forces both medium trigger (1074) and short trigger (1072) to also pivot toward pistol grip (1024). Additionally, pivoting medium trigger (1074) toward pistol grip (1024) forces short trigger (1072) to pivot toward pistol grip (1024), but does not force long trigger (1076) to pivot toward pistol grip (1024). Pivoting short trigger (1072) toward pistol grip (1024) does not force longer trigger (1076) or medium trigger (1074) to pivot toward pistol grip (1024). In some other versions, triggers (1072, 1074, 1076) are arranged such that pivotal movement of one trigger (1072, 1074, 1076) does not necessarily force pivotal movement of any other trigger (1072, 1074, 1076). In such versions, the operator may nevertheless pivot more than one trigger (1072, 1074, 1076) simultaneously by engaging more than one trigger (1072, 1074, 1076) with the operator's hand.

Button (1062) is positioned to be actuated by trigger (1072) when short trigger (1072) pivots toward pistol grip (1024). Button (1064) is positioned to be actuated by medium trigger (1074) when medium trigger (1074) pivots toward pistol grip (1024). Button (1066) is positioned to be actuated by long trigger (1076) when long trigger (1076) pivots toward pistol grip (1024). While buttons (1062, 1064, 1066) are located along pistol grip (1024) in the present example, buttons (1062, 1064, 1066) may instead be located along any suitable location of handle assembly (1020) in order to make selective contact with triggers (1072, 1074, 1076), respectively, when triggers (1072, 1074, 1076) are pivoted toward pistol grip (1024). In the present example, each trigger (1072, 1074, 1076) is independently capable of pivoting clamp arm (144) toward blade (160). Thus, clamp arm (144) may be pivoted toward blade (160) regardless of which trigger (1072, 1074, 1076) or combination of triggers (1072, 1074, 1076) is pivoted toward pistol grip (1024). In some other versions, only one or two of triggers (1072, 1074, 1076) is operable to pivot clamp arm (144) toward blade (160). In such examples, the other trigger (1072, 1074, 1076) or triggers (1072, 1074, 1076) merely activates/activate an energized state at end effector (140) (e.g., vibration of blade (160) and/or application of RF electrosurgical energy through end effector (140), etc.).

Buttons (1062, 1064, 1066) are in electrical communication with circuit board (34) in order to control various functions of instrument (100) when buttons (1062, 1064, 1066) are pressed or released by triggers (1072, 1074, 1076). FIGS. 19A-19D show one such example. As shown in FIG. 19A, trigger assembly (1028) is in an open position, such that short trigger (1072), medium trigger (1074), and long trigger (1076) are not in contact with respective buttons (1062, 1064, 1066). As shown in FIG. 19B, the operator may pivot the entire trigger assembly (1028) toward pistol grip (1024) such that short trigger (1072) makes contact with button (1062), medium trigger (1074) makes contact with button (1064), and long trigger (1076) makes contact with button (1072). Clamp arm (144) closes toward blade (160) as triggers (1072, 1074, 1076) pivot toward the position of FIG. 19B. With all three buttons (1062, 1064, 1066) being activated, circuit board (34) activates transducer (112) to drive blade (160) to vibrate ultrasonically at a high level of power.

In some versions, handle assembly (1020) includes one or more tactile feedback features and/or latching features that provide tactile feedback and/or selectively lock triggers (1072, 1074, 1076) in place when triggers (1072, 1074, 1076) reach the position shown in FIG. 19B. In the present example, handle assembly (1020) transitions directly from the state shown in FIG. 19A to the state shown in FIG. 19B. In some other instances, handle assembly (1020) may transition from the state shown in FIG. 19C or the state shown in FIG. 19D to the state shown in FIG. 19B. It should therefore be understood that the operator may adjust the power level of ultrasonic blade (160) while tissue is being compressed against blade (160) by clamp arm (144).

FIG. 19C shows handle assembly (1020) in a state where only triggers (1072, 1074) have been pivoted toward pistol grip (1024). Again, clamp arm (144) closes toward blade (160) as triggers (1072, 1074) pivot toward the position of FIG. 19C. With only buttons (1062, 1064) being activated, circuit board (34) activates transducer (112) to drive blade (160) to vibrate ultrasonically at a medium level of power.

In some versions, handle assembly (1020) includes one or more tactile feedback features and/or latching features that provide tactile feedback and/or selectively lock triggers (1072, 1074) in place when triggers (1072, 1074) reach the position shown in FIG. 19C. In the present example, handle assembly (1020) transitions directly from the state shown in FIG. 19A to the state shown in FIG. 19C. In some other instances, handle assembly (1020) may transition from the state shown in FIG. 19B or the state shown in FIG. 19D to the state shown in FIG. 19C. It should therefore be understood that the operator may adjust the power level of ultrasonic blade (160) while tissue is being compressed against blade (160) by clamp arm (144).

FIG. 19D shows handle assembly (1020) in a state where only trigger (1072) has been pivoted toward pistol grip (1024). Again, clamp arm (144) closes toward blade (160) as trigger (1072) pivots toward the position of FIG. 19D. With only button (1062) being activated, circuit board (34) activates transducer (112) to drive blade (160) to vibrate ultrasonically at a low level of power. In some versions, handle assembly (1020) includes one or more tactile feedback features and/or latching features that provide tactile feedback and/or selectively lock trigger (1072) in place when trigger (1072) reaches the position shown in FIG. 19D. In the present example, handle assembly (1020) transitions directly from the state shown in FIG. 19A to the state shown in FIG. 19D. In some other instances, handle assembly (1020) may transition from the state shown in FIG. 19B or the state shown in FIG. 19B to the state shown in FIG. 19D. It should therefore be understood that the operator may adjust the power level of ultrasonic blade (160) while tissue is being compressed against blade (160) by clamp arm (144).

In some exemplary variations, handle assembly (1020) is incorporated into an instrument with an end effector that is operable to apply RF electrosurgical energy to tissue, in addition to or as an alternative to being operable to apply ultrasonic energy to tissue. In some such variations, at least one button (1062, 1064, 1066) may be configured to trigger the activation of one or more RF electrosurgical electrodes in the end effector. In other words, at least one trigger (1072, 1074, 1076) may be specifically associated with activating RF electrosurgical features. In addition or in the alternative, handle assembly (1020) may be incorporated into an instrument with an end effector that has a translating knife member instead of ultrasonic blade (160). Such a translating knife member may be configured to sever tissue and may be driven by a motor. In such versions, at least one button (1062, 1064, 1066) may be configured to trigger the activation of the motor. In other words, at least one trigger (1072, 1074, 1076) may be specifically associated with driving the knife member to sever tissue. Other suitable variations will be apparent to those of ordinary skill in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) an end effector, wherein the end effector is configured to operate at a first energy level and at a second energy level, wherein the end effector is further configured to transition between an open position and a closed position, wherein the end effector is configured to grasp tissue in the closed position; and (b) a handle assembly, wherein the handle assembly comprises: (i) a body, (ii) a trigger pivotally coupled to the body, wherein the trigger is configured to pivot in a first direction relative to the body to actuate the end effector from the open position to the closed position, and (ii) an activation element, wherein the activation element is in communication with the end effector, wherein the activation element is configured to activate the end effector at either the first energy level or the second energy level, wherein the trigger is configured to either activate the activation element or determine whether the end effector operates at the first energy level or the second energy level.

Example 2

The surgical instrument of Example 1, wherein the trigger is configured to pivot in the first direction to a first position, wherein the trigger is configured to pivot further in the first direction to a second position, wherein the end effector is configured to operate at the first energy level when the trigger is located at the first position, wherein the end effector is configured to operate at the second energy level when the trigger is located at the second position.

Example 3

The surgical instrument of Example 2, wherein the body further comprises a first switch and a second switch, wherein the trigger is configured to activate the first switch when the trigger reaches the first position, wherein the trigger is configured to activate the second switch when the trigger reaches the second position.

Example 4

The surgical instrument of any one or more of Examples 2 through 3, wherein the body comprises a Hall Effect sensor, wherein the trigger comprises a magnet, wherein the Hall Effect sensor is configured to determine if the trigger is in the first position or the second position.

Example 5

The surgical instrument of any one or more of Examples 2 through 4, wherein the body comprises a force transducer, wherein the force transducer is configured to determine if the trigger is in the first position or the second position.

Example 6

The surgical instrument of any one or more of Examples 1 through 5, wherein the body comprises a damping system, wherein the activation element is coupled with the damping system, wherein the damping system is configured to prevent activation of the activation element if the trigger contacts the activation element at a velocity above a threshold.

Example 7

The surgical instrument of any one or more of Examples 1 through 6, wherein the body further comprises: (i) a pistol grip defining a first slot and a second slot, (ii) a first movable button housed within the first slot, wherein the first movable button is configured to move from an activated state to a deactivated state, and (iii) a second movable button housed within the second slot, wherein the second movable button is configured to move from an activated state to a deactivated state.

Example 8

The surgical instrument of Example 7, wherein the trigger is configured to pivot in the first direction toward the pistol grip to contact the first moveable button or the second movable button when the first moveable button or the second movable button are in the activated state.

Example 9

The surgical instrument of Example 8, wherein the first movable button is configured to rotate about a pivot in the first slot.

Example 10

The surgical instrument of any one or more of Examples 8 through 9, wherein the first movable button is configured to alter the functionality of the end effector when the trigger contacts the first movable button in the activated state.

Example 11

The surgical instrument of any one or more of Examples 1 through 10, wherein the trigger comprises a first grip and a second grip, wherein the first grip is configured to actuate the end effector from the open position to the closed position, wherein the second grip is configured to activate the activation element.

Example 12

The surgical instrument of Example 11, wherein the first grip is configured to move independently of the second grip.

Example 13

The surgical instrument of any one or more of Examples 11 through 12, wherein the first grip and the second grip are configured to travel together though a first range of motion, wherein the second grip is configured to travel through a second range of motion independent of the first grip.

Example 14

The surgical instrument of any one or more of Examples 1 through 13, wherein the trigger is further configured to move in a second direction relative to the body, wherein the trigger is configured to determine whether the end effector operates at the first energy level or the second energy level based on a position of the trigger in the second direction.

Example 15

The surgical instrument of Example 14, wherein the body further comprise a mode selection frame, wherein a portion of the trigger is housed within the mode selection frame.

Example 16

The surgical instrument of Example 15, wherein the mode selection frame comprises a mode selection channel, a first energy channel, and a second energy channel, wherein the portion of the trigger housed within the mode selection frame is configured to travel in the mode selection channel when the trigger moves in the second direction, wherein the portion of the trigger housed within the mode selection frame is configured to travel in either the first energy channel or the second energy channel when the trigger moves in the first direction.

Example 17

The surgical instrument of Example 16, wherein the trigger is configured to pivot relative to the body while moving in the second direction.

Example 18

A surgical instrument, comprising: (a) an end effector, wherein the end effector is configured to operate at a first energy level and at a second energy level, wherein the end effector is further configured to transition between an open position and a closed position, wherein the end effector is configured to grasp tissue in the closed position; and (b) a handle assembly, wherein the handle assembly comprises: (i) a body comprising a first button, a second button, and a third button, wherein each button is configured to provide a respective activated state of the end effector, and (ii) a trigger assembly pivotally coupled to the body, wherein the trigger assembly further comprises: (A) a first trigger configured pivot from a first open position to a first closed position, wherein the first trigger is configured to contact the first button in the first closed position, (B) a second trigger configured to pivot from a second open position to a second closed position, wherein the second trigger is configured to contact the second button in the second closed position, wherein the second trigger is shorter than the first trigger, and (C) a third trigger configured to pivot from a third open position to a third closed position, wherein the third trigger is configured to contact the third button in the third closed position, wherein the third trigger is short than the second trigger.

Example 19

The surgical instrument of Example 18, wherein at least one of the first trigger, the second trigger, or the third trigger is further operable to transition the end effector from the open position to the closed position.

Example 20

A surgical instrument, comprising: (a) an end effector, wherein the end effector is configured to operate at a first energy level and at a second energy level, wherein the end effector is further configured to transition between an open position and a closed position, wherein the end effector is configured to grasp tissue in the closed position; and (b) a handle assembly, wherein the handle assembly comprises: (i) a body, (ii) a trigger pivotally coupled to the body, wherein the trigger is configured to pivot in a first direction relative to the body to actuate the end effector from the open position to the closed position, wherein the trigger is configured to actuate in a second direction relative to the body to select whether the end effector operates at the first energy level or the second energy level, and (ii) an activation element, wherein the activation element is in communication with the end effector, wherein the activation element is configured to activate the end effector at either the first energy level or the second energy level.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
(a) an end effector, wherein the end effector is configured to transition from an open position toward a closed position, wherein the end effector is configured to grasp tissue in the closed position, wherein the end effector is configured to transition from an inactive state toward an active state;
(b) a handle assembly, wherein the handle assembly comprises:
(i) a body,
(ii) a trigger assembly pivotally coupled to the body, wherein the trigger assembly comprises:
(A) a first trigger configured to independently pivot from a first open position toward a first closed position in order to drive the end effector from the open position toward the closed position, respectively, and
(B) a second trigger configured to pivot from a second open position toward a second closed position, wherein the second trigger is configured to activate the end effector at a second power level while the second trigger is in the second closed position and the first trigger is in the first closed position, wherein the second trigger is configured to drive the first trigger into the first closed position while the second trigger actuates toward the second closed position,
wherein the first trigger is configured to activate the end effector at a first power level while the first trigger is in the first closed position and the second trigger is in the second open position.

2. The surgical instrument of claim 1, wherein the body further comprises a pistol grip.

3. The surgical instrument of claim 2, wherein the first trigger is interposed between the pistol grip and the second trigger.

4. The surgical instrument of claim 2, further comprising a first button disposed on the pistol grip, wherein the first trigger is configured to contact the first button in the first closed position.

5. The surgical instrument of claim 4, further comprising a second button disposed on the pistol grip, wherein the second trigger is configured to contact the second button in the second closed position.

6. The surgical instrument of claim 1, wherein the first power level is different than the second power level.

7. The surgical instrument of claim 1, wherein the trigger assembly further comprises a third trigger configured to pivot from a third open position toward a third closed position in order to transition the end effector from the inactive state toward the active state, respectively.

8. The surgical instrument of claim 7, wherein the second trigger is interposed between the first trigger and the third trigger.

9. The surgical instrument of claim 7, wherein the first trigger is shorter than the second trigger, wherein the first trigger is wider than the second trigger.

10. The surgical instrument of claim 9, wherein the second trigger is shorter than the third trigger, wherein the third trigger is narrower than the second trigger.

11. The surgical instrument of claim 1, wherein the end effector is rotatable relative to the handle assembly.

12. The surgical instrument of claim 1, further comprising a transducer assembly coupled to the handle assembly.

* * * * *